US012582425B2

(12) United States Patent
Mintz et al.

(10) Patent No.: US 12,582,425 B2
(45) Date of Patent: Mar. 24, 2026

(54) CATHETER INCLUDING A RADIOPAQUE EXPANDABLE MEMBER

(71) Applicant: Covidien LP, Mansfield, MA (US)

(72) Inventors: Eric Mintz, Costa Mesa, CA (US); Ujwal Jalgaonkar, Irvine, CA (US); Syamala Rani Pulugurtha, Irvine, CA (US); Athanasios Touris, Santa Ana, MA (US); Kevin V. Nguyen, Westminster, CA (US); Xiaodong Ma, Acton, MA (US); Edwin Wang, Tustin, CA (US)

(73) Assignee: Covidien LP, Mansfield, MA (US)

( * ) Notice: Subject to any disclaimer, the term of this patent is extended or adjusted under 35 U.S.C. 154(b) by 288 days.

(21) Appl. No.: 17/111,266

(22) Filed: Dec. 3, 2020

(65) Prior Publication Data

US 2022/0175404 A1 Jun. 9, 2022

(51) Int. Cl.
| | |
|---|---|
| *A61B 17/22* | (2006.01) |
| *A61M 25/00* | (2006.01) |
| *A61M 25/01* | (2006.01) |

(52) U.S. Cl.
CPC ... *A61B 17/22031* (2013.01); *A61M 25/0045* (2013.01); *A61M 25/0053* (2013.01); *A61M 25/0108* (2013.01); *A61B 2017/22079* (2013.01); *A61M 2205/0266* (2013.01)

(58) Field of Classification Search
CPC .. A61F 2/9525; A61F 2/9522; A61M 25/0082
See application file for complete search history.

(56) References Cited

U.S. PATENT DOCUMENTS

| | | | |
|---|---|---|---|
| 7,094,243 B2 | 8/2006 | Mulholland et al. | |
| 8,366,735 B2 | 2/2013 | Bose et al. | |
| 2013/0018387 A1* | 1/2013 | Diamant | A61B 17/221 |
| | | | 606/127 |
| 2013/0253474 A1 | 9/2013 | Farhangnia et al. | |
| 2014/0074144 A1 | 3/2014 | Shrivastava et al. | |
| 2016/0151080 A1* | 6/2016 | Sase | A61B 17/221 |
| | | | 606/127 |
| 2016/0228134 A1 | 8/2016 | Martin et al. | |
| 2017/0303949 A1* | 10/2017 | Ribo Jacobi | A61B 17/12109 |
| 2018/0161121 A1 | 6/2018 | Butler et al. | |
| 2018/0193043 A1* | 7/2018 | Marchand | A61F 2/013 |

(Continued)

OTHER PUBLICATIONS

Kim et al., "Printing ferromagnetic domains for untethered fast-transforming soft materials," Nature, vol. 558, Jun. 14, 2018, 18 pp.

(Continued)

*Primary Examiner* — Kathleen S Holwerda
*Assistant Examiner* — Serenity A Miller
(74) *Attorney, Agent, or Firm* — Shumaker & Sieffert, P.A.

(57) ABSTRACT

In some examples, a catheter includes an elongated body and an expandable member at a distal portion of the elongated body and defining at least part of a distal tip of the catheter. The expandable member is formed from materials that enable a distal tip of the catheter to be radiopaque without the addition of a separate radiopaque marker (e.g., a solid metal ring of radiopaque material separate from and connected to the elongated body) at the distal tip of the catheter.

24 Claims, 7 Drawing Sheets

(56) References Cited

U.S. PATENT DOCUMENTS

| | | | |
|---|---|---|---|
| 2018/0250498 A1 * | 9/2018 | Stern | A61M 25/0054 |
| 2019/0269491 A1 | 9/2019 | Jalgaonkar et al. | |

OTHER PUBLICATIONS

Extended Search Report from counterpart European Application No. 21209588.9 dated Apr. 29, 2022, 10 pp.
Response to Communication pursuant to Rule 69 and Inivitation pusuant to Rule 70a(1) EPC dated Jun. 13, 2022, from European Application No. 21209588.9, filed Aug. 8, 2022, 91 pp.

* cited by examiner

80 — INTRODUCE CATHETER INTO VASCULATURE OF PATIENT

82 — DEPLOY EXPANDABLE MEMBER

84 — ASPIRATE THROMBUS

CATHETER INCLUDING A RADIOPAQUE EXPANDABLE MEMBER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

This disclosure describes example catheters including an elongated body and an expandable member at a distal portion of the elongated body and defining at least part of a distal tip of the catheter. The expandable member is configured to expand radially outward within a hollow anatomical structure (e.g., a blood vessel) of a patient, e.g., to engage a thrombus. The expandable member is formed from materials that enable a distal tip of the catheter to be radiopaque without the addition of a separate radiopaque marker (e.g., a solid metal ring of radiopaque material separate from and connected to the elongated body) at the distal tip of the catheter, e.g., proximal to the expandable member. A solid metal radiopaque marker band may contribute to the overall stiffness of a distal tip of a catheter. Forming the expandable member from a radiopaque material may enable the solid metal radiopaque marker to be eliminated from the distal tip of the catheter, thereby enabling the distal tip of the catheter to be more flexible. In addition, because the expandable member is formed from a radiopaque material, a longer extent of the distal tip of the catheter may be visible under fluoroscopy or x-ray imaging. This may provide a clinician with a better indication of a location of the distal tip within a patient.

In some examples, the expandable member is formed from a plurality of structural elements (e.g., drawn-filled tubes), each structural element comprising an outer first material surrounding an inner core comprising a second material, where the first material is more radiopaque than the second material, or where the second material is more radiopaque than the first material. For example, the expandable member may include a braided structure comprising interwoven structural elements. As another example, the expandable member may include a stent-like expandable frame defined by struts, each strut being formed from a structural element. In other examples, the expandable member includes a braided structure comprising first filaments of a first material interwoven with second filaments of a second material, wherein the second material is more radiopaque than the first material.

In some examples in which an expandable member of a catheter is formed from a radiopaque material, the catheter is devoid of any separate radiopaque markers at a distal tip of the elongated body, e.g., anywhere along the expandable member. For example, a radiopaque marker band may be located at a more-proximal portion of the catheter, such as proximal to the expandable member, but not distal to a proximal end of the expandable member. In other examples, the catheter is devoid of any solid metal radiopaque marker bands anywhere along the catheter.

This disclosure also describes examples of methods of forming the catheters described herein and methods of using the catheters.

Clause 1: In some examples, a catheter includes an elongated body having a proximal body portion and a distal body portion, and defining a body inner lumen; and an expandable member located at the distal body portion, the expandable member defining an expandable member inner lumen, the expandable member inner lumen including a distal extension of the body inner lumen, wherein the expandable member is configured to expand radially outward and thereby expand the expandable member inner lumen radially outward, wherein the expandable member includes a plurality of structural elements, one or more of the structural elements of the plurality of structural elements including a first material surrounding a core including a second material, and wherein the first material is more radiopaque than the second material, or wherein the second material is more radiopaque than the first material.

Clause 2: In some examples of the catheter of clause 1, the expandable member is configured to self-expand radially outward from a collapsed configuration to an expanded configuration.

Clause 3: In some examples of the catheter of clause 1 or clause 2, the catheter includes a radiopaque marker band located at a junction between the elongated body and the expandable member.

Clause 4: In some examples of the catheter of any of clauses 1 through 3, an outer diameter of the expandable member while the expandable member is in an expanded configuration is greater than an outer diameter of the elongated body.

Clause 5: In some examples of the catheter of any of clauses 1 through 4, the expandable member defines a cylindrical tube when in an expanded configuration.

Clause 6: In some examples of the catheter of clause 5, a distal end of the cylindrical tube forms a distal mouth of the catheter when the expandable member is in the expanded configuration.

Clause 7: In some examples of the catheter of clause 5 or clause 6, when the expandable member is in the expanded configuration, an outer diameter of the cylindrical tube is greater than an outer diameter of the distal body portion, wherein the outer diameter of the cylindrical tube is no more than 300% of the outer diameter of the distal body portion.

Clause 8: In some examples of the catheter of any of clauses 5 through 7, the cylindrical tube has an axial length of about 0.5 centimeters to about 3.0 centimeters while the expandable member is in the expanded configuration.

Clause 9: In some examples of the catheter of any of clauses 5 through 8, the expandable member includes a tapered section at a proximal end of the cylindrical tube when the expandable member is in the expanded configuration.

Clause 10: In some examples of the catheter of clause 9, the expandable member further includes a proximal section at a proximal end of the tapered section, wherein an outer diameter of the proximal section is substantially equal to an outer diameter of the distal body portion of the elongated body.

Clause 11: In some examples of the catheter of any of clauses 5 through 10, the cylindrical tube defines a distal-most section of the expandable member.

Clause 12: In some examples of the catheter of any of clauses 1 through 11, the first material includes an electroplated coating on an exterior surface of the core.

Clause 13: In some examples of the catheter of any of clauses 1 through 12, one or more structural elements of the plurality of structural elements includes a drawn-filled tube.

Clause 14: In some examples of the catheter of any of clauses 1 through 13, the plurality of structural elements include filaments interwoven into a braided structure.

Clause 15: In some examples of the catheter of any of clauses 1 through 14, the plurality of structural elements include struts defining an expandable frame.

Clause 16: In some examples of the catheter of any of clauses 1 through 15, the elongated body further includes: an inner liner; a structural support member; and an outer jacket, wherein the structural support member is positioned between the inner liner and the outer jacket.

Clause 17: In some examples of the catheter of clause 16, the structural support member includes a coil and a braid disposed over at least a portion of the coil.

Clause 18: In some examples of the catheter of clause 17, the expandable member extends over at least a portion of the coil.

Clause 19: In some examples of the catheter of any of clauses 16 through 18, the structural support member includes a coil, and the expandable member extends over at least a portion of the coil.

Clause 20: In some examples of the catheter of any of clauses 16 through 19, the inner liner extends distally past a proximal end of the expandable member.

Clause 21: In some examples of the catheter of any of clauses 1 through 20, the distal body portion includes a plurality of concentric layers, and a proximal end of the plurality of structural elements of the expandable member forms one of the concentric layers along an axial length of the distal body portion.

Clause 22: In some examples of the catheter of clause 21, the concentric layers of the distal body portion include a structural support member having a distal end, and a proximal end of the plurality of structural elements of the expandable member is located distal of the distal end of the structural support member.

Clause 23: In some examples of the catheter of clause 22, the proximal end of the plurality of structural elements and the structural support member are substantially radially equidistant from a central longitudinal axis of the catheter.

Clause 24: In some examples of the catheter of any of clauses 1 through 23, the catheter does not have a solid metal radiopaque marker band distal to a proximal end of the expandable member.

Clause 25: In some examples of the catheter of any of clauses 1 through 24, the first material includes a nickel-titanium alloy, and wherein the second material includes platinum or a platinum alloy.

Clause 26: In some examples of the catheter of any of clauses 1 through 25, the first material includes gold, and the second material includes a nickel-titanium alloy.

Clause 27: In some examples of the catheter of any of clauses 1 through 26, the expandable member further includes a flexible membrane coupled to the plurality of structural elements.

Clause 28: In some examples of the catheter of clause 27, the flexible membrane at least partially covers an inner surface or an outer surface of the plurality of structural elements.

Clause 29: In some examples of the catheter of clause 27 or clause 28, the flexible membrane includes a fluid-impermeable polymer.

Clause 30: In some examples of the catheter of any of clauses 27 through 29, the flexible membrane is radiopaque.

Clause 31: In some examples of the catheter of clause 30, the flexible membrane includes a thermoplastic elastomer combined with a radiopaque material.

Clause 33: In some examples of the catheter of any of clauses 1 through 31, the expandable member is configured to axially contract in response to an application of a suction force to the proximal body portion of the elongated body.

Clause 34: In some examples of the catheter of any of clauses 1 through 32, the expandable member has an axial length of about 0.5 centimeters to about 3.0 centimeters.

Clause 35: In some examples of the catheter of any of clauses 1 through 33, when the expandable member is in an expanded configuration, a greatest outer diameter of the expandable member is greater than an outer diameter of the distal body portion, and the outer diameter of the cylindrical tube is no more than 300% of the outer diameter of the distal body portion.

Clause 36: In some examples of the catheter of any of clauses 1 through 34, while a suction force is applied to the body inner lumen, the expandable member is configured to axially contract in response to contact with a thrombus enabling a user to observe, via fluoroscopic imagery, that the catheter is engaged with the thrombus.

Clause 37: In some examples, a system includes an introducer sheath; the catheter of claim 1; and a compression tool configured to compress the expandable member for insertion of the catheter into the introducer sheath.

Clause 38: In some examples, a catheter includes an elongated body including a proximal body portion and a distal body portion, and a body inner lumen passing through the elongated body; and an expandable member located at the distal body portion, the expandable member forming an expandable member inner lumen passing therethrough, the expandable member inner lumen including a distal extension of the body inner lumen, wherein the expandable member is configured to self-expand radially outward and thereby expand the expandable member inner lumen radially outward, wherein the expandable includes a plurality of first filaments including a first material interwoven with a plurality of second filaments including a second material, and wherein the second material is more radiopaque than the first radiopaque material.

Clause 39: In some examples of the catheter of clause 38, the catheter does not include a solid metal radiopaque marker band at the distal portion of the elongated body.

Clause 40: In some examples of the catheter of clause 38, the first material includes a nickel-titanium alloy, and wherein the second material includes platinum or a platinum alloy.

Clause 41: In some examples, a catheter includes an elongated body including a proximal body portion and a distal body portion, and defining a body inner lumen; and a radiopaque expandable member connected to a distal portion of the elongated body, the expandable member defining an expandable member inner lumen in fluid communication with the body inner lumen, wherein the expandable member is configured to expand from a collapsed configuration to an expanded configuration, and wherein, while a suction force is applied to the body inner lumen and the expandable member inner lumen, the expandable member is configured to axially contract in response to contact with a thrombus.

Clause 42: In some examples of the catheter of clause 41, the expandable member includes a plurality of structural elements, wherein one or more of the structural elements of the plurality of structural elements includes a first material surrounding a core including a second material, and wherein the first material is more radiopaque than the second material, or wherein the second material is more radiopaque than the first material.

Clause 43: In some examples of the catheter of clause 41, the expandable member is configured to be navigated through vasculature of the patient while the expandable member is in the expanded configuration.

Clause 44: In some examples of the catheter of clauses 41 or clause 42, the expandable member defines a cylindrical tube when in the expanded configuration.

Clause 45: In some examples of the catheter of any of clauses 41 through 43, the expandable member further includes a flexible membrane coupled to a plurality of structural elements.

Clause 46: In some examples of the catheter of clause 45, the flexible membrane includes a thermoplastic elastomer combined with a radiopaque material.

Clause 47: In some examples, a method of aspirating a thrombus includes distally advancing the catheter of any of clauses 1-46 from an introducer sheath within a vasculature of a patient toward the thrombus; applying cyclical aspiration to axially contract and expand the expandable member; and proximally withdrawing the catheter from the vasculature of the patient.

Clause 48: In some examples of the method of clause 47, while the expandable member is in an expanded configuration, an outer diameter of the expandable member is smaller than an inner diameter of a vessel of the patient at an intended site of treatment, and distally advancing the catheter within the vasculature of the patient includes distally advancing the catheter within the vasculature of the patient while the expandable member is in the expanded configuration.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

6

Figure 8:
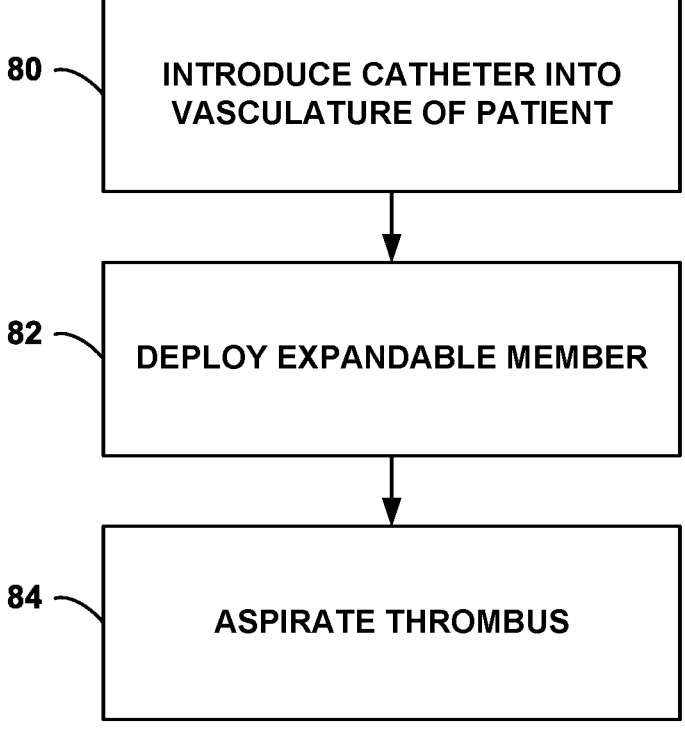

FIG. 8 is a flow diagram of an example method of using a catheter.

DETAILED DESCRIPTION

The disclosure describes a medical device, referred to herein as a "catheter," including an expandable member configured to expand radially outward within a hollow anatomical structure (e.g., a blood vessel) of a patient, e.g., to engage with a thrombus to facilitate aspiration of the thrombus (or other material or object(s) to be removed, such as a plaque or foreign body). Some catheters include a distinct radiopaque marker band (e.g., a solid metal ring) near a distal tip of the catheter, which may facilitate placement of the catheter via fluoroscopic imaging. This radiopaque marker band may also contribute to an overall (e.g., excessive) stiffness of the distal tip of the catheter, which may adversely impact navigability of the catheter to distal sites in the vasculature of a patient. According to the examples of this disclosure, the expandable members described herein can be integrally formed from one or more materials that enable a distal tip or portion of the catheter to be radiopaque without the addition of a separate, more-rigid radiopaque marker band (e.g., a solid metal radiopaque marker band), thereby improving the flexibility of the distal tip and improving the navigability of the catheter. In addition, because a length of the expandable member is formed from a radiopaque material as compared to a separate, smaller or shorter (as measured in a direction parallel to a longitudinal axis of the catheter) radiopaque marker band, a longer portion of the distal tip or distal portion of the catheter (e.g., about 1 centimeter to about 10 centimeters) may be visible under fluoroscopy or x-ray imaging, thereby providing a clinician with a better indication of a location of the distal tip or distal portion within the vasculature of the patient.

Example catheters in accordance with this disclosure include a relatively flexible elongated body configured to be navigated through vasculature of a patient, e.g., tortuous vasculature in a brain of the patient. The elongated body may include a plurality of concentric layers, such as an inner liner, an outer jacket, and a structural support member (e.g., a coil, braid, and/or hypotube) positioned between at least a portion of the inner liner and outer jacket. A distal tip or distal portion of the catheter includes an expandable member, such as an expandable stent-like structure or an expandable braid, positioned distal to a distal portion of the elongated body. In some examples, the expandable member is distinct from, but mechanically coupled to, the distal portion of the elongated body. In other examples, the expandable member is integrally formed with (e.g., laminated with and/or forming a distal extension of) the distal portion of the elongated body. The expandable member is configured to expand radially outward within a hollow anatomical structure (e.g., a blood vessel) of the patient. This may enable, for example, the expandable member to engage with a thrombus, such as a clot, embolism, or other material such as plaques or foreign bodies during an aspiration procedure, such as, but not limited to, a medical procedure using A Direct Aspiration first Pass Technique (ADAPT) for acute stroke thrombectomy.

The expandable member may help improve aspiration of the thrombus into the catheter by providing a relatively large luminal diameter (and therefore exert a larger aspiration force against the thrombus or other material to be removed) and interior space for the thrombus to engage with the catheter compared to examples in which an otherwise similar catheter does not include an expandable member. For example, such a catheter that does not include an expandable member may have limited radial expansion due to a structural support member that extends to the distal end of the catheter, and may thus make it harder to aspirate a thrombus (e.g., due to a smaller cross-sectional dimension of the distal end of the catheter). The expandable member may overcome such radial expansion limitations, thereby increasing thrombus engagement, reducing the amount of time required for revascularization, and increasing revascularization success rates for various procedures, as compared to similar procedures performed using catheters that do not include an expandable member to engage a thrombus.

In some examples, the radiopacity of the expandable member is provided by a plurality of structural elements from which the expandable element is formed, some or all of the structural elements comprising an outer first material surrounding an inner core comprising a second material, where the first material is more radiopaque than the second material, or wherein the second material is more radiopaque than the first material. For example, some or all of the structural elements can comprise a wire or filament, which can take the form of a drawn-filled tube. In some examples, the expandable member includes a braided structure comprising braided or interwoven filaments, some or all of the filaments being formed from such a structural element. In other examples, the expandable member may include a stent-like expandable frame defined by struts, each strut being formed from a structural element.

In other examples, in addition to, or instead of, the aforementioned structural elements, the radiopacity of the expandable member is provided by radiopaque structural elements combined with less radiopaque or even radiotransparent structural elements. For example, the expandable element can include a braided structure comprising first filaments of a first material interwoven with second filaments of a second material, where either the first material or the second material is more radiopaque than the other (e.g., where one of the two materials is radiopaque and the other is not radiopaque, or where both materials are radiopaque but one is more radiopaque than the other). In other examples, the expandable element includes a multi-coaxial-layered laser-cut stent, wherein at least one of the coaxial layers includes a material that is radiopaque.

Figure 1:
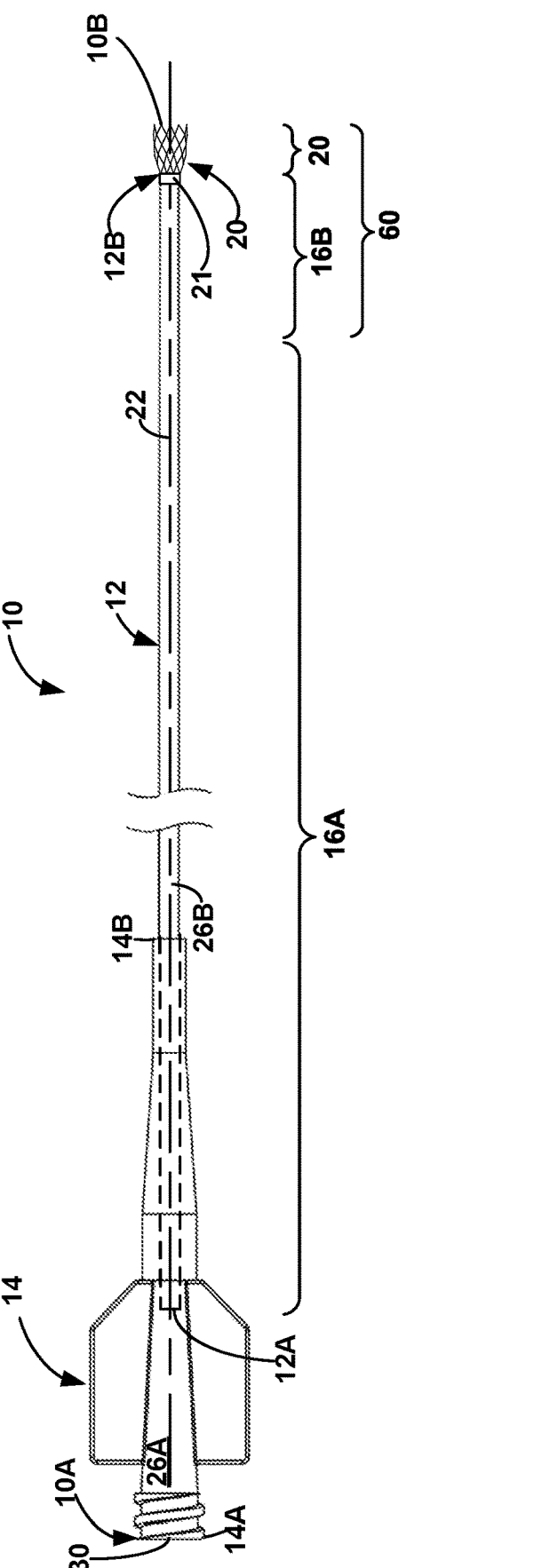
FIG. 1 is a conceptual side view of an example catheter, which includes an elongated body and an expandable member at a distal portion of the elongated body.
Figure 2:
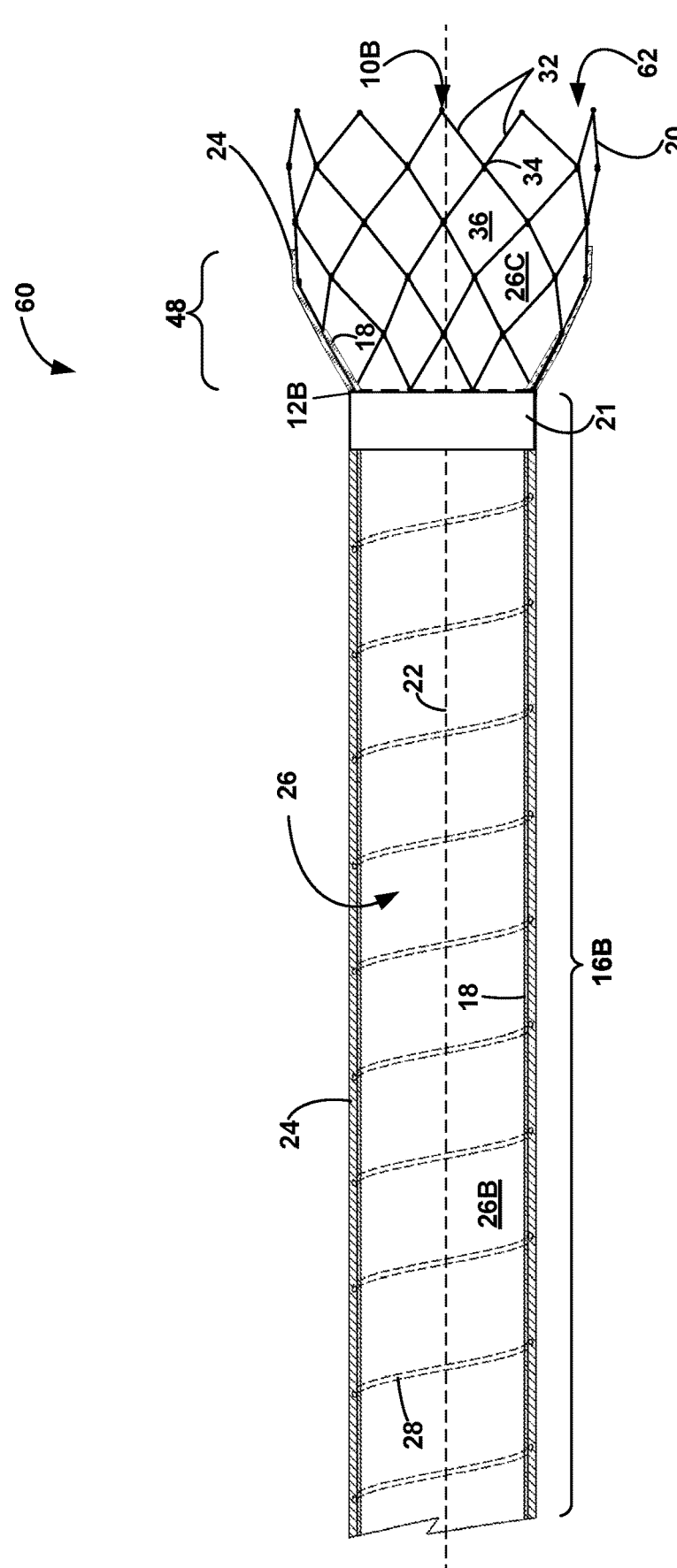
FIG. 2 is a conceptual cross-sectional view of an example of the distal tip of the catheter of FIG. 1, including the distal portion of the elongated body and the expandable member, where the cross-section is taken through a center of the catheter and along a longitudinal axis.

FIG. 1 is a conceptual side view of an example catheter 10, and FIG. 2 is a conceptual cross-sectional view of a distal tip or distal portion 60 of the example catheter 10. As shown in FIGS. 1 and 2, catheter 10 can include an elongated body 12, a hub 14, and an expandable member 20. Catheter 10 defines an inner lumen 26, including a hub lumen 26A, a body lumen 26B, and an expandable member lumen 26C.

Elongated body 12 is configured to be advanced through vasculature of a patient via a pushing force applied to proximal body portion 16A (e.g., via hub 14) of elongated body 12 without buckling, kinking, or otherwise undesirably deforming (e.g., ovalization). As shown in FIG. 2, elongated body 12 can include a plurality of concentric layers, such as an inner liner 18, an outer jacket 24, and a structural support member 28 positioned between at least a portion of inner liner 18 and at least a portion of outer jacket 24. Elongated body 12 includes a proximal body portion 16A and a distal body portion 16B, which are each longitudinal sections of elongated body 12 and do not overlap in the longitudinal direction (along longitudinal axis 22). Elongated body 12 extends from body proximal end 12A to body distal end 12B and defines at least one body lumen 26B (also referred to as a body inner lumen). In the example shown in FIG. 1, proximal end 12A of elongated body 12 is received within hub 14 and is mechanically connected to hub 14 via an adhesive, welding, or another suitable technique or combination of techniques. Inner lumen 26 of catheter 10 may be defined by portions of hub 14, inner liner 18, and expandable member 20.

Catheter 10 may be used as an aspiration catheter to remove a thrombus or other material such as plaques or foreign bodies from vasculature of a patient. In such examples, a suction force (e.g., a vacuum) may be applied to proximal end 10A of catheter 10 (e.g., via hub 14) to draw a thrombus or other blockage into inner lumen 26. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, catheter 10 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated body 12 may be structurally configured to be relatively flexible, pushable, and relatively kink- and buckle-resistant, so that it may resist buckling when a pushing force is applied to a relatively proximal section of catheter 10 (e.g., via hub 14) to advance elongated body 12 distally through vasculature, and so that it may resist kinking when traversing around a tight turn in the vasculature. In some examples, elongated body 12 is configured to substantially conform to the curvature of the vasculature. In addition, in some examples, elongated body 12 has a column strength and flexibility that allow at least distal body portion 16B of elongated body 12 to be navigated from a femoral artery, through the aorta of the patient, and into the intracranial vascular system of the patient, e.g., to reach a relatively distal treatment site.

Although primarily described as being used to reach relatively distal vasculature sites, catheter 10 may also be configured to be used with other target tissue sites. For example, catheter 10 may be used to access tissue sites throughout the coronary and peripheral vasculature, the gastrointestinal tract, the urethra, ureters, fallopian tubes, veins and other hollow anatomical structures of a patient.

In some examples, a "working length" of catheter 10 may be measured from distal end 14B of hub 14 (e.g., a distal end of a strain relief member of a hub assembly) to distal end 10B of catheter 10 along longitudinal axis 22. The working length of catheter 10 may depend on the location of the target tissue site within the body of a patient or may depend on the medical procedure for which catheter 10 is used. For example, if catheter 10 is a distal access catheter used to access vasculature in a brain of a patient from a femoral artery access point at the groin of the patient, catheter 10 may have a working length of about 115 centimeters (cm) to about 145 cm or more, such as about 130 cm, although other lengths may be used. The distal tip or distal portion 60 of catheter 10, including distal body portion 16B of elongated body 12 and expandable member 20, may be about 5 cm to about 35 cm in length. Proximal body portion 16A of elongated body 12 may be about 90 cm to about 130 cm in length, depending on the length of distal tip or distal portion 60.

Expandable member 20 is configured to radially expand within a vessel of a patient, e.g., to engage a thrombus within the vessel. Expandable member 20 is positioned at (e.g., overlapping with or entirely distal to) distal body portion 16B of elongated body 12, such that a distal end of expandable member 20 defines distal end 10B of catheter 10 and a distal mouth 62 open to inner lumen 26 of catheter 10. For example, expandable member lumen 26C (also referred to as an expandable member inner lumen) forms a distal extension of the inner lumen 26B of the elongated body 12. In these examples, expandable member lumen 26C is in fluid communication with inner lumen 26B of the elongated body 12.

Expandable member 20 can include a frame configured to expand radially outward, thereby expanding lumen 26C radially outward. The frame of expandable member 20 can be formed from at least two different materials (e.g., two different chemical compositions), one of which is more radiopaque than the other, which can be less radiopaque or radiotransparent. For example, the expandable frame can enable expandable member 20 to maintains its expanded shape (after it is expanded), even in the presence of a suction force applied to inner lumen 26 of catheter 10 during an aspiration process. Example expandable frames include an expandable stent-like structure or an expandable tubular braid or weave, which can each be formed from a plurality of structural elements, each structural element comprising a first material surrounding a core comprising a second material, where the first material is more radiopaque than the second material, or wherein the second material is more radiopaque than the first material. For example, each structural element can comprise a wire or filament, which can take the form of a drawn-filled tube. In some examples, the expandable member includes a braided structure comprising interwoven filaments, each filament being formed from such a structural element. In other examples, the expandable frame of expandable member 20 may be formed from radiopaque structural elements combined with less radiopaque or even radiotransparent structural elements.

In any of these examples, expandable member 20 may include a flexible membrane 48 coupled to (e.g., radially inward and/or radially outward of) the expandable frame, or integrated into the expandable frame. In some examples, flexible membrane 48 may be formed of an elastomeric material, such as polyolefin thermoplastic elastomers, polyurethane elastomeric alloys or silicone, that permits the expansion of expandable member 20. In other examples, expandable member 20 does not include such flexible membrane 48.

Instead of or in addition to including a relatively small (e.g., relatively short or narrow, as measured in an axial direction, along longitudinal axis 22) radiopaque marker band, such as a solid metal radiopaque ring or partial ring, located at a distal portion or tip of the catheter, in examples described herein, a radiopaque material extends across or throughout a substantial portion of a longitudinal length of expandable member 20 (e.g., along a length parallel to longitudinal axis 22). Such configurations enable a solid metal radiopaque marker band to be eliminated from the distal tip of catheter 10 while still enabling the distal tip of catheter 10 to be radiopaque, which may provide one or more advantages over a catheter including a solid radiopaque marker band at the distal tip. For example, a solid metal radiopaque marker band may be formed from a relatively rigid ring of metal (e.g., platinum-iridium), and may contribute to the overall stiffness of a distal tip or portion of a catheter. Forming expandable member 20 from a solid metal radiopaque material may enable such a stiff radiopaque marker band to be eliminated from the distal tip or portion of catheter 10, thereby enabling the distal tip or portion 60 of catheter 10 to be more flexible. In addition, by eliminating the rigid radiopaque marker band, a distal tip or portion 60 of catheter 10 may be less rigid and more easily expand or neck down for delivery into vasculature of a patient through a sheath. This increased radial flexibility (e.g., range of expandability in a radial direction) may be useful, for example, when a relatively smaller introducer catheter is required for insertion via certain vasculature access sites, such as the radial artery. As one non-limiting example, a radial access sheath may have an inner diameter of about 5 French, as compared to about 6 French for femoral access sheaths. Accordingly, a smaller diameter (or other maximum cross-sectional dimension) catheter 10 may be useful for such applications.

Incorporating the radiopaque material throughout the axial length of expandable member 20 enables a longer extent of the distal tip or portion 60 of catheter 10 (e.g., about 1 centimeters to about 10 centimeters, such as about 2 centimeters to about 6 centimeters) to be visible under fluoroscopy or x-ray imaging. This may provide a clinician with a better indication of a location of the distal tip or portion 60 within a patient. In addition, expandable member 20 formed from a radiopaque material may be fluoroscopically illuminated, enabling the clinician to monitor the shape of expandable member 20 as the clinician navigates expandable member 20 through the patient's vasculature. For example, the radiopaque material may enable the clinician to observe when expandable member 20 is bending or not bending around a curve in the patient's vasculature. As another example, the radiopaque material may allow the clinician to observe if expandable member 20 becomes kinked or otherwise deformed in an undesirable manner that may inhibit navigation of catheter 10 through the vasculature. A radiopaque marker band alone, on the other hand, would not enable a shape of expandable member 20 to be visible under fluoroscopy or x-ray imaging.

In addition, by incorporating a radiopaque material throughout expandable member 20, a clinician may be able to more-easily discern when the distal mouth 62 of expandable member 20 has come into contact with a thrombus within the vasculature of a patient. For example, the clinician may distally advance expandable member 20 through the vasculature of the patient toward a thrombus. When the mouth 62 of expandable member 20 contacts the thrombus, the thrombus may form a seal over the distal mouth 62 of expandable member 20. In the presence of a suction force (e.g., via an aspiration pump) applied to inner lumen 26 of catheter 10, such a seal over the mouth 62 of expandable member 20 may cause expandable member 20 to partially axially contract and/or otherwise change shape along longitudinal axis 22. Expandable member 20 may be configured to partially axially contract and/or otherwise change shape when engaged with a thrombus due to its relative flexibility, e.g., compared to expandable members that include a solid metal radiopaque marker band. Due to the radiopaque material of expandable member 20, the clinician may easily observe this axial contraction of expandable member 20 on a fluoroscopic imaging screen, informing the clinician when catheter 10 has engaged the thrombus.

In some, but not all, examples, catheter 10 includes a more rigid radiopaque marker band (e.g., a solid metal radiopaque ring or partial ring) proximal to expandable member 20 along elongated body 12. For example, as shown in FIG. 1, catheter 10 may include a marker band 21 located at the distal end of elongated body 12, e.g., at the junction between elongated body 12 and expandable member 20. Marker band 21 can be entirely proximal to a proximal end of expandable member 20 in some examples. Marker band 21 may improve the durability of the joint between the elongated body 12 and expandable member 20, and may also act as a locator point to help a clinician identify the proximal end of expandable member 20 within fluoroscopic imagery. For example, expandable member 20 alone, though radiopaque, may be relatively less radiopaque than marker band 21. Accordingly, marker band 21 may help a clinician to more quickly locate expandable member 20 within the fluoroscopic imagery.

In some examples, in its expanded states, expandable member 20 defines a tubular, cylindrical, or funnel shape configured to provide catheter 10 with a relatively large diameter (or other maximum cross-sectional diameter) distal end 10B (compared to, for example, proximal body portion 16A of elongated body 12) and interior space 26C for better engagement with a thrombus (e.g., clot or embolus). In some examples, the cross-section of expandable member 20 in its expanded state may be round (e.g., circular) and the cross-sectional axis may be referred to as a diameter. In some examples, the cross-section may be irregularly shaped, in which case the cross-sectional dimension may be referred to as the major axis (e.g., a longest dimension of the cross-section). In the expanded configuration, the cross-section of expandable member 20 may be wider at a distal end than a proximal end. For example, in the expanded configuration, the inner diameter at the distal end of expandable member 20 (e.g., along all or part of distal section 20C of expandable member (FIG. 3) and/or at distal opening 62) may be about 150 percent to about 300 percent wider than an inner diameter of expandable member 20 near distal body portion 16B of elongated body 12.

In some examples, such as the examples shown in FIGS. 1 and 2, expandable member 20 may resemble a stent-like structure that includes a tubular body comprising a plurality of struts 32 (e.g., an individual straight portion of an undulating ring) that are interconnected via one or more connections at adjacent vertices 34 (peaks or valleys) to define a plurality of cells 36 between adjacent struts 32, such as diamond-shape cells or other cell designs. In general, each of the struts 32 of expandable member 20 may be a substantially straight portion (e.g., a straight or nearly straight member) that may join with one or more other struts 32 at a respective vertex 34. Struts 32 may be forced apart and radially outward from one another (e.g., via straightening of the undulating rings) to increase the diameter at various portions of expandable member 20. In other examples, expandable member 20 may include an expandable braid, an expandable mesh (e.g., woven sleeve or woven tubular structure), or other design.

Expandable member 20 can be configured to facilitate thrombus removal. In examples in which catheter 10 is used with an aspiration procedure (e.g., ADAPT technique), the size and shape of expandable member 20 may enable catheter 10 to better engage a thrombus by increasing the distal opening 62 into which the thrombus may be received, increasing the total aspiration force exerted on the thrombus via a larger luminal area, and/or by distributing the aspiration forces over a greater portion of the thrombus rather than a localized area, thereby allowing the thrombus to be aspirated into catheter 10 more effectively. Expandable member

20 enables catheter 10 to maintain a relatively small diameter elongated body 12 (e.g., within proximal body portion 16A) to facilitate navigability of catheter 10, while also enabling catheter 10 to exhibit improved engagement and suction force characteristics that may be attributed to having a large-diameter distal end 10B. In some examples, the presence of expandable member 20 may lead to improved revascularization success rates, such as due to the improved thrombus engagement and/or suction (e.g., to better pull the entirety of the thrombus into catheter 10 during aspiration) as described herein.

In addition, expandable member 20 can be configured to exhibit a relatively low longitudinally compressive stiffness, which can facilitate thrombus removal. For example, when combined with cyclical aspiration, in which suction force applied to inner lumen 26 of catheter 10 is varied over time, the relatively low longitudinally compressive stiffness of expandable member 20 may enable the expandable member 20 to undergo "flutter"-type motion, in which expandable member 20 alternatingly contracts and expands in an axial direction (e.g., parallel to longitudinal axis 22), e.g. at a periodic frequency. This cyclical longitudinal contraction and expansion of expandable member 20 can in turn cause cyclical axial motion of the distal mouth 62 relative to the (stationary or relatively stationary) thrombus, which may facilitate dislodgment of the thrombus from vasculature. Additionally, as the expandable member 20 contracts longitudinally rather than radially in response to the application of cyclical aspiration, distal mouth 62 of expandable member 20 may remain more open and engaged with the thrombus, thereby further facilitating removal of the thrombus.

Expandable member 20 may be of any suitable length and diameter, which may be selected based on the target vessel or particular procedure being performed. For example, expandable member 20 may be made be long enough to fully engulf a thrombus (e.g., an average amount of thrombus material), but short enough to avoid excessive friction between an outer surface of expandable member 20 and an inner surface of an introducer sheath or an outer catheter. In some examples, expandable member 20 may be about 2 centimeters to about 25 centimeters long, measured in a direction parallel to longitudinal axis 22. For example, expandable member 20 may be about 1.5 cm, about 2.0 cm, or about 25 cm in length, such as from about 0.5 cm to about 3.0 cm.

As discussed above, in some examples, in the collapsed state, a distal section of expandable member 20 may have a cross-sectional dimension substantially equal to (e.g., equal to or nearly equal to) or less than the outer diameter of elongated body 12 proximate to expandable member 20. In some examples in which expandable member 20 defines a tube shape or a cylinder shape (having an open distal mouth 62) in an expanded state, expandable member 20 may define a substantially constant diameter (e.g., constant or nearly constant in the absence of forces compressing expandable member 20) along about 0.5 cm to about 3 cm, or 0.5 cm to about 2.5 cm of a length of expandable member 20, which can be a distal-most length in some examples. The length of expandable member 20 can be selected to be long enough to engulf a thrombus, but short enough to enable catheter 10 to be inserted into and/or withdrawn from a patient via an outer sheath. An expandable member that is too long may exert too much friction that interferes with movement of catheter 10 into or out of a patient via a sheath.

In some examples, in the expanded configuration, distal end 10B of expandable member 20 is larger than the outer diameter of elongated body 12, but smaller than the inner diameter of the target vasculature of the patient, such that expandable member 20 may be advanced through the vasculature of the patient while in the expanded configuration. Expandable member 20 may, for example, be configured to be in an expanded configuration within the vasculature of a patient without engaging with the vessel walls around an outer perimeter of expandable member 20, which may facilitate navigation of the expanded expandable member 20 through the vasculature. In some examples, distal end 10B of expandable member 20 may be about 110 percent to about 300 percent of the diameter of the proximal end of expandable member 20. In some examples, the expanded outer diameter or the cross-sectional dimension of expandable member 20 at distal end 10B may be about 110 percent to about 130 percent of the diameter of elongated body 12. As one illustrative example, catheter 10 may include an elongated body 12 with an inner diameter of about 0.074 inches (about 0.188 cm) and an outer diameter of about 0.086 inches (about 0.218 cm), and an expandable member 20 having, in the expanded configuration, a maximum inner diameter of about 0.090 inches (about 0.229 cm) and a maximum outer diameter of about 0.098 inches (about 0.249 cm), corresponding to an expansion of the diameter of expandable member 20 to about 114 percent of the diameter of elongated body 12. In other examples, expandable member may expand to about 200 percent, 250 percent, 300 percent, or another larger percentage of the outer diameter or cross-sectional dimension of a portion of elongated body 12.

In some examples, the expandability of expandable member 20 at distal tip or portion 60 may allow the cross-sectional dimension of elongated body 12 within proximal body portion 16A to remain comparatively small. As described above, such a combination may allow catheter 10 to exhibit the improved navigability characteristics of a catheter body with a small diameter while still providing catheter 10 with the improved engagement and suction characteristics that may be attributed to having a large-diameter distal end 10B.

In some examples, an inner surface of expandable member 20 may comprise a surface treatment configured to promote at least one of mechanical or chemical engagement between the inner surface and the thrombus, and enable the thrombus to be pulled into lumen 26 of catheter 10 more effectively. For example, a coating may be applied to portions of the inner surface of expandable member 20 (e.g., the inner surface of the struts or braided filaments, or a flexible membrane 48 if present), where the coating has a relatively high clot affinity. Such affinity may be measured, for example, with a dynamic mechanical analyzer (DMA) equipped with a shear sandwich clamp. Examples of suitable coating materials to increase the affinity of the thrombus to expandable member 20 may include, for example, a thermoplastic elastomer such as ChronoPrene™ (AdvanSource Biomaterials, Wilmington, Massachusetts), ChronoPrene™ (AdvanSource Biomaterials, Wilmington, Massachusetts), ChronoPrene™ 5A, ChronoPrene™ 15A; a polyolefin elastomer such as ethylene-octene or ethylene-butene copolymer, for example, ENGAGE™ Polyolefin Elastomers (Dow Chemical Company, Midland, Michigan), ENGAGE™ 8107, 7367, 7270; or the like.

As another example, portions of the inner surface of expandable member 20 may be textured via etching or otherwise roughened (or rougher) in comparison to the outer surface of the expandable member 20 to better mechanically engage the thrombus. In some examples, an inner surface of expandable member 20 can include a polymer that is etched to promote mechanical thrombus engagement.

In some examples, thrombus engagement with expandable member 20 may be enhanced by delivering electrical energy to expandable member 20. For example, a source of electrical energy (e.g., an electrical signal generator) may deliver an electrical signal to expandable member 20 via one or more electrical conductors (not shown) electrically coupled to expandable member 20. The electrical energy may be positively charged to electrostatically engage a thrombus. Characteristics of the electrical energy may be adjusted to better engage the thrombus, such as polarity, or an amount or type of current delivered. For example, pulsed direct current may be employed, optionally with a non-square and/or non-negative waveform. The electrical conductors can extend through inner lumen 26B of elongated body 12, can extend along an outer surface of elongated body 12, can be embedded in a wall of elongated body 12, or have any other suitable configuration.

Expandable member 20 may expand from a collapsed configuration to an expanded configuration using any suitable technique. In some examples, expandable member 20 may be balloon-expandable. For example, once elongated body 12 is positioned within the vessel of a patient adjacent a target treatment site, a balloon (not shown) may be introduced through lumen 26 of catheter 10 and inflated to radially expand expandable member 20 from a collapsed configuration to an expanded configuration. Once in the expanded configuration, expandable member 20 may maintain its shape to allow the balloon to be deflated and removed. Expandable member 20 may then be collapsed for removal from the vessel of the patient by, for example, pulling elongated body 12 or at least expandable member 20 into an outer sheath having an inner lumen with a diameter less than the outer diameter of an expanded expandable member 20. The outer sheath may apply an inward force to expandable member 20 as expandable member 20 is retracted proximally into the outer sheath.

In other examples, expandable member 20 may be configured to self-expand. For example, the expandable frame of expandable member 20 may be formed from a metal, and may include a shape-memory material such as Nitinol (and, optionally, additional material(s) or metal(s) such as radiopaque material(s) or metal(s)). In some such examples as described further below, an outer sheath can be positioned over expandable member 20 to retain expandable member 20 in a collapsed configuration, e.g., during navigation of elongated body 12 to a target treatment site within the vasculature of a patient. Once at the target treatment site, the outer sheath can be retracted or elongated body 12 may be extended distally outward from the sheath to allow expandable member 20 to self-expand. In other examples, catheter 10 may be navigated through vasculature with expandable member 20 in an expanded state.

In other examples, an electrical energy may be used to expand expandable member 20. For example, expandable member 20 (or a portion or a layer thereof) may be formed from a material or metal that bends or deflects in response to a current passed therethrough (or to heat generated as a result of such current). One such type of material is shape memory alloy actuator material, e.g. nitinol or Flexinol™ available from Dynalloy, Inc. of Irvine, California USA.

Hub 14 may be positioned at (e.g., proximal to or at least partially overlapping with) a proximal body portion 16A of elongated body 12. Proximal end 14A of hub 14 may define the catheter proximal end 10A of catheter 10 and may include an opening 30 aligned with inner lumen 26B of elongated body 12, such that inner lumen 26B of elongated body 12 may be accessed via opening 30 and, in some examples, closed via opening 30. For example, hub 14 may include a luer connector, a hemostasis valve, or another mechanism or combination of mechanisms for connecting hub 14 to another device such as a vacuum source for performing the aspiration techniques described herein. In some examples, proximal end 10A of catheter 10 can include another structure in addition to, or instead of, hub 14.

In some examples, inner liner 18 of elongated body 12 defines at least a portion 26B of inner lumen 26 of catheter 10, inner lumen 26B defining a passageway through elongated body 12. In some examples, inner lumen 26B may extend over the entire length of inner liner 18 (e.g., from proximal end 12A of elongated body 12 to the distal end 12B). Inner lumen 26B may be sized to receive a medical device (e.g., another catheter, a guidewire, an embolic protection device, a stent, or any combination thereof), a therapeutic agent, or the like. Elongated body 12, alone or with inner liner 18 and/or other structures, may define a single inner lumen 26, or multiple inner lumens (e.g., two inner lumens or three inner lumens 26A-26C) of catheter 10.

Inner lumen 26B formed at least by inner liner 18 may define the inner diameter of elongated body 12. The diameter of inner lumen 26B (as measured in a direction perpendicular to a longitudinal axis 22 of elongated body 12) may vary based on the one or more procedures with which catheter 10 may be used. In some examples, the diameter of inner lumen 26B of elongated body 12 may be substantially constant (e.g., constant or nearly constant) from proximal end 12A to distal end 12B or may taper (gradually or more step-wise) from a first inner diameter at proximal end 12A to a second, smaller inner diameter at distal end 12B. As described further below, the inner diameter of expandable member 20 may be larger than the inner diameter of elongated body 12 proximal to expandable member 20 while expandable member 20 is in an expanded configuration.

Inner liner 18 may be formed using any suitable material, such as, but not limited to, polytetrafluoroethylene (PTFE), expanded PTFE (ePTFE, e.g., unidirectional ePTFE or bidirectional ePTFE), a fluoropolymer, perfluoroalkyoxy alkane (PFA), fluorinated ethylene propylene (FEP), polyolefin elastomers or any combination thereof. A unidirectional ePTFE may be stretched in one of the longitudinal or radial directions, and a bi-directional ePTFE may be stretched in both the longitudinal and radial directions. Other examples of materials from which inner liner 18 may be formed include, but are not limited to, Low Density Polyethylene (LDPE) (e.g., about 42 D), a PTFE having a durometer of about 60 D, High Density Polyethylene (HDPE), or any combination thereof. Some such polyolefin materials may have similar coefficients of friction as PTFE and may be conducive to processing.

In some examples, one or more portions of the inner surface of inner liner 18 defining inner lumen 26B (and in some examples, the inner surface of expandable member 20 defining inner lumen 26C) may be lubricious to facilitate the introduction and passage of a medical device (e.g., another catheter, a guide member, an embolic protection device, a stent, a thrombectomy device, or any combination thereof), a therapeutic agent, a thrombus, or the like, through lumen 26B. A lubricious inner liner 18 may also enable relatively easy tracking of elongated body 12 over a guide member (e.g., a guidewire or a microcatheter). In some examples, the material from which portions of inner liner 18 is formed may itself be lubricious (e.g., PTFE). In addition to, or instead of, being formed from a lubricious material, in some examples, an inner surface of inner liner 18 is coated with a lubricious coating such as a hydrophilic coating.

Elongated body 12 includes one or more structural support members 28 positioned over inner liner 18. Structural support member 28 is configured to increase the structural integrity of elongated body 12 while allowing elongated body 12 to remain relatively flexible. For example, structural support member 28 may be configured to help elongated body 12 substantially maintain its cross-sectional shape (e.g., circular or nearly circular) or at least help prevent elongated body 12 from buckling or kinking as it is navigated through tortuous anatomy. Additionally, or alternatively, structural support member 28, together with inner liner 18, and outer jacket 24, may help distribute both pushing and rotational forces along a length of elongated body 12, which may help prevent kinking of elongated body 12 upon rotation of body 12 or help prevent buckling of body 12 upon application of a pushing force to body 12. As a result, a clinician may apply pushing forces, rotational forces, or both, to the proximal portion of elongated body 12, and such forces may cause a distal portion of elongated body 12 to advance distally, rotate, or both, respectively.

Structural support member 28 may include one or more tubular braided structures, one or more coil members defining a plurality of turns, e.g., in the shape of a helix, or a combination of one or more braided structures and one or more coil members. Thus, although the examples of the disclosure primarily describe structural support member 28 as a coil, in other examples, catheter 10 may include a braided structure instead of a coil, a braided structure in addition to a coil, or a combination that includes one or more of each structure. As one example, a proximal portion of structural support member 28 may include a braided structure and a distal portion of structural support member 28 may include a coil member.

Structural support member 28 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 28 may include one or more metal wires braided or coiled around inner liner 18. The metal wires may include round wires, flat-round wires, flat wires, or any combination thereof.

In other examples, structural support member 28 may include a spiral-cut hypotube that is positioned over inner liner 18. Structural support member 28 may extend along only a portion of a length of elongated body 12 and is positioned proximal to expandable member 20. In some examples, the distal end of structural support member 28 may abut the proximal end of expandable member 20 and may be coupled to expandable member 20 (e.g., mechanically coupled or bonded with adhesive, or welded). In other examples, expandable member 20 may not be coupled to structural support member 28 or may not be in direct contact (e.g., abutting contact) with structural support member 28, although the two members may be in the same radial layer of elongated body 12 (and/or have the same inner diameter and/or outer diameter where structural support member 28 and expandable member 20 meet or come closest to each other in the longitudinal direction). For example, the distal end of structural support member 28 may be adjacent to the proximal end of expandable member 20 but separated by a small gap. In such examples, structural support member 28 and expandable member 20 may be in the same radial layer and inner liner 18, outer jacket 24, or both may secure both expandable member 20 and structural support member 28 in place along elongated body 12.

In some examples, structural support member 28 may be coupled, adhered, or mechanically connected to at least a portion of an outer surface of inner liner 18. For example, structural support member 28 may be positioned over inner liner 18 and secured in place (e.g., fixed) relative to inner liner 18 by outer jacket 24 using a melt-reflow/heat shrink process, via adhesives or other suitable technique.

Additionally or alternatively, structural support member 28 may be secured to inner liner 18 with the assistance of a support layer (not shown) that helps adhere structural support member 28 to one or both of inner liner 18 and outer jacket 24. The support layer may include a thermoplastic material or a thermoset material, such as a thermoset polymer or a thermoset adhesive that bonds to inner liner 18, outer jacket 24, or both. In some cases, the material forming the support layer may have elastic properties, such that there may be a tendency for the support layer to return to a resting position. In some examples, the support layer is positioned over the entire length of structural support member 28 and inner liner 18. In other examples, the support layer is only positioned over a part of the length of structural support member 28 and inner liner 18.

Elongated body 12 can also include outer jacket 24 positioned over structural support member 28 and inner liner 18, the structural support member 28 being positioned between portions of inner liner 18 and outer jacket 24. In some examples, outer jacket 24 may be positioned around structural support member 28 such that outer jacket 24 covers at least a part or all of both inner liner 18 and structural support member 28. Outer jacket 24, together with inner liner 18 and structural support member 28, may be configured to define elongated body 12 having the desired structural characteristics (e.g., flexibility, kink resistance, torque responsiveness, structural integrity, pushability, and column strength, which may be a measure of a maximum compressive load that can be applied to elongated body 12 without taking a permanent set). For example, outer jacket 24 may have stiffness characteristics that contribute to the desired stiffness profile of elongated body 12.

In some examples, outer jacket 24 may be formed to have a stiffness that decreases from a proximal end 12A of elongated body 12 toward distal end 12B. The lowered stiffness of outer jacket 24 within the distal body portion 16B of elongated body 12 may improve the flexibility and navigability of catheter 10 through tortious vasculature of the patient, while the relatively higher stiffness of outer jacket 24 within the proximal body portion 16A of catheter 10 may provide better pushability or kink resistance. In some examples, outer jacket 24 may be formed from two or more different materials with different mechanical properties that enable outer jacket 24 to exhibit the desired stiffness characteristics. In some examples outer jacket 24 may define a stiffness that is greater than the stiffness of flexible membrane 48 of expandable member 20.

In some examples, outer jacket 24 may be formed using any suitable material including, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer (e.g., a thermoplastic, elastomeric polymer configured to accommodate radial expansion of expandable member 20), polyurethanes, polyamides, or other thermoplastic material, or combinations thereof.

Outer jacket 24 may be heat shrunk around structural support member 28 and, in some examples, at least a portion (e.g., a proximal portion) of expandable member 20 to secure the two members 20, 28 in the same radial layer. In some examples, during the heat shrinking of outer jacket 24 around structural support member 28, the material of outer jacket 24 may flow into at least some of the inner spacings or gaps (e.g., gaps between the adjacent turns of the coils, or between the struts or braids) within structural support member 28 or expandable member 20 such that portions of outer jacket 24, structural support member 28, and/or expandable member 20 form a laminated structure.

In some examples, at least a portion of an outer surface of outer jacket 24 and/or expandable member 20 includes one or more coatings, such as, but not limited to, an anti-thrombogenic coating, which may help reduce the formation of thrombi in vitro, an anti-microbial coating, and/or a lubricating coating. In some examples, the lubricating coating may be configured to reduce static friction or kinetic friction between elongated body 12 and tissue of the patient as elongated body 12 is advanced through the vasculature. In addition, or instead, in some examples, the lubricating coating may be configured to reduce static or kinetic friction between elongated body 12 and another catheter through which elongated body 12 may be inserted. The lubricating coating can be, for example, a hydrophilic coating. In some examples, the entire working length of elongated body 12 (from distal end 14B of hub 14 to the distal end of outer jacket 24) may be coated with the hydrophilic coating. In other examples, only a portion of the working length of elongated body 12 coated with the hydrophilic coating. This may provide a length of elongated body 12 distal from distal end 14B of hub 14 with which the clinician may grip elongated body 12, e.g., to rotate elongated body 12, pull elongated body 12 when removing elongated body 12 from the patient, or push elongated body 12 through vasculature.

Although a coating or another material may be applied over the outer surface of outer jacket 24, outer jacket 24 may still substantially define shape and size of the outer surface of elongated body 12. In some examples, the outer diameter of elongated body 12 may be substantially constant (e.g., constant or nearly constant) along the length of elongated body 12. In other examples, the outer diameter of elongated body 12 may taper from the first outer diameter within proximal body portion 16A of elongated body 12 to a second outer diameter at a point proximate to the proximal end of expandable member 20.

In some examples, expandable member 20 may be mechanically coupled to structural support member 28 and/or layered between (at least in a proximal portion of the expandable member 20) inner liner 18 and outer jacket 24. For example, expandable member 20 and structural support member 28 can be formed independently of one another, and the proximal end of expandable member 20 may be coupled to the distal end of structural support member 28. In some examples, expandable member 20 and structural support member 28 may be joined via welding, brazing, soldering, adhesives, epoxy, or other suitable technique. In some examples, expandable member 20 may be welded, soldered, bonded, or hooked to structural support member 28. In some examples, expandable member 20 comprises a plurality of struts 32 that define a plurality of cells 36. One or more of the proximal peaks of the proximal-most strut (e.g., at the proximal end of expandable member 20) may be coupled to structural support member 28 such that expandable member 20 is mechanically coupled to structural support member 28 at a plurality of circumferential positions around structural support member 28, such as shown in FIG. 2. In some examples, expandable member 20 may be bonded (e.g., glued), hooked (e.g., mechanically interlocked), or coupled to structural support member 28 using other means.

In some examples, structural support member 28 and expandable member 20 may be integrally formed. In some such examples, at least a proximal portion 20A of expandable member 20 and structural support member 28 form the same radial layer of catheter 10, or in other words, are radially equidistant from central longitudinal axis 22. For example, structural support member 28 may include a plurality of wires (e.g., coils or braids) that are subsequently woven to form expandable member 20, such that the manufacture may not necessarily require welding or other assembly or connection of expandable member 20 to structural support member 28. In other examples, structural support member 28 and expandable member 20 may be formed using the same hypotube; the proximal portion of the hypotube being spirally cut to form a somewhat coil-like structure (e.g. structural support member 28) while the distal portion of the hypotube is cut to form a plurality of interconnected struts that form expandable member 20.

Additionally, or alternatively, expandable member 20 may be at least partially secured to structural support member 28 via inner liner 18 and/or outer jacket 24. For example, expandable member 20 may not be directly coupled to structural support member 28 or may not be in direct contact (e.g., abutting contact) with structural support member 28, although the two members may be in the same radial layer of catheter 10. In an example, expandable member 20 may be positioned adjacent to structural support member 28 over inner liner 18, and outer jacket 24 may be positioned over expandable member 20 and structural support member 28. Outer jacket 24 may be heat shrunk over the two members such that outer jacket 24 secures both expandable member 20 and structural support member 28 in place relative to inner liner 18. In such examples, expandable member 20 may be positioned at least partially between inner liner 18 and outer jacket 24 (e.g., layered or positioned between an inner and outer flexible membrane 48, wherein flexible membrane 48 includes extensions of inner liner 18 and outer jacket 24).

For example, at least a proximal portion of expandable member 20 may be positioned between inner liner 18 and outer jacket 24. One or both of inner liner 18 or outer jacket 24 may extend over the entire length of expandable member 20 or may extend over only a portion of the length of expandable member 20. For example, flexible membrane 48 may include a distal portion of inner liner 18 extending over only part of the length of expandable member 20 leaving portions of expandable member 20 exposed to inner lumen 26C. The exposed portions of expandable member 20 may provide better engagement with a thrombus and/or prevent distal migration of thrombus from catheter 10 due to the texture of expandable member 20 or direct electrostatic engagement with expandable member 20. For example, as described herein, elongated body 12 may comprise an electrical conductor electrically coupled to expandable member 20, and expandable member 20 may be configured to receive an electrical signal via the conductor that causes expandable member 20 to electrostatically engage the thrombus. In some examples, expandable member 20 may be configured to expand radially outward in response to receiving the electrical signal.

In some examples, both inner liner 18 and outer jacket 24 terminate proximal to a distal end of expandable member 20. In other examples, inner liner 18 and outer jacket 24 can have other arrangements relative to expandable member 20.

Figure 3:
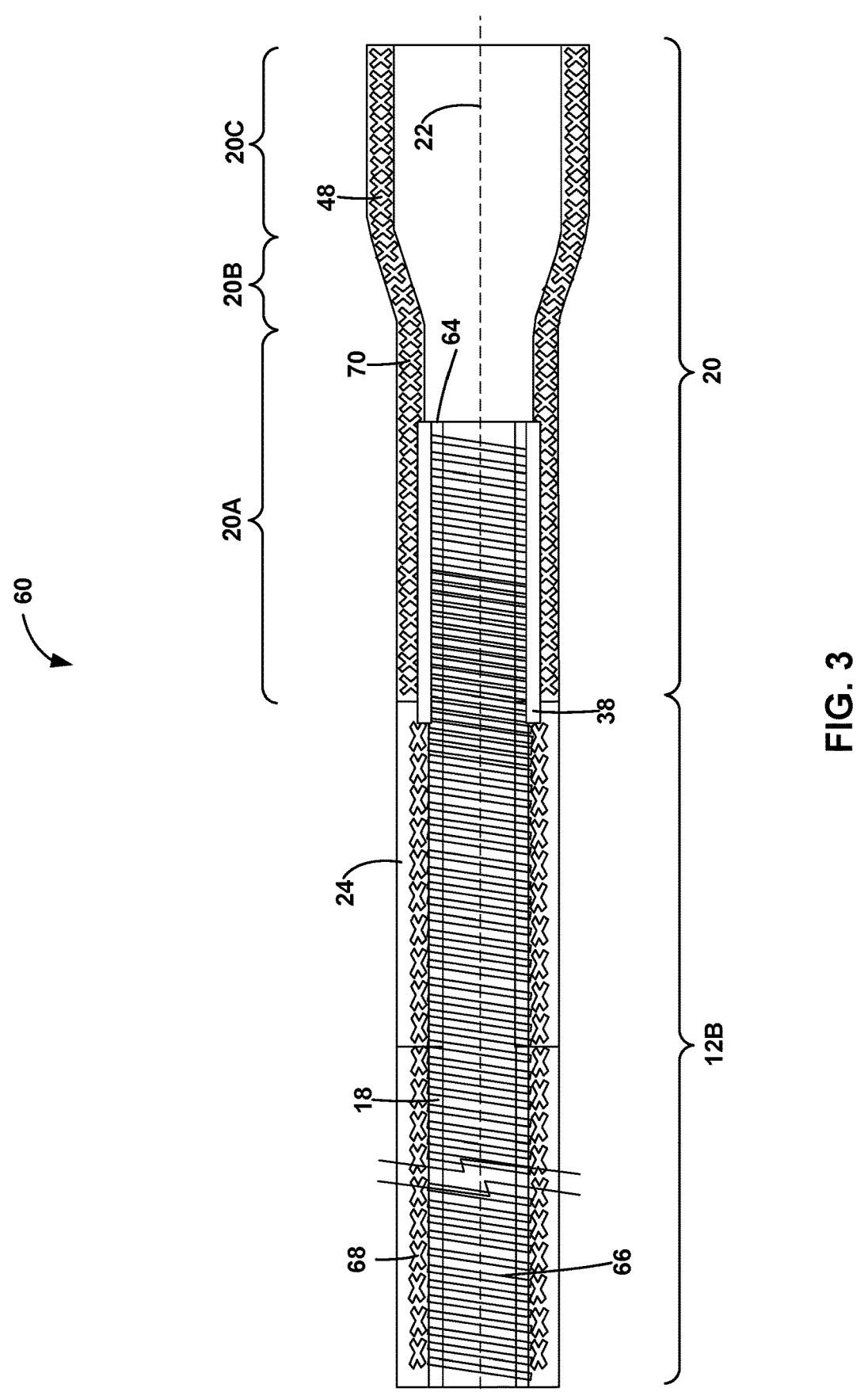
FIG. 3 is a conceptual cross-sectional view of another example of the distal tip of the catheter of FIG. 1, where the cross-section is taken through a center of the catheter and along a longitudinal axis.

Expandable member 20 may include any suitable arrangement relative to inner liner 18, outer jacket 24, and structural support member 28. For example, FIG. 3 is a conceptual cross-sectional view of another example of the distal tip or portion 60 of catheter 10 of FIG. 1, where the cross-section is taken through a center of the catheter and along a longitudinal axis 22. As shown in FIG. 3, distal tip or portion 60 includes distal end 12B of elongated body 12 and expandable member 20, including parts of inner liner 18, outer jacket 24, a coiled support member 66 ("structural coil 66"), and a braided structural support member 68 ("structural braid 68"). Coiled support member 66 and structural braid 68 are individually or collectively examples of structural support member 28 of FIGS. 1 and 2. Accordingly, one or both of coil 66 and braid 68 may be omitted in practicing the catheter 10 of FIG. 3, or other catheters disclosed herein.

Expandable member 20 can include an expandable frame, e.g. in the form of an expandable, generally tubular weave or braid 70 ("expandable braid 70") and a liquid barrier layer, e.g. in the form of a relatively thin and flexible membrane 48, coupled to the expandable frame. In some examples, where both structural coil 66 and structural braid 68 are present, structural braid 68 does not overlap (e.g., in an axial direction parallel to longitudinal axis 22) with expandable braid 70, whereas structural coil 66 may overlap with both structural braid 68 and expandable braid 70.

In the example shown in FIG. 3, flexible membrane 48 of expandable member 20 includes an inner layer 64, which in some examples, but not all examples, may be a distal extension of inner liner 18 of elongated body 12 that extends distally to (e.g., to a location radially inward of) at least a proximal portion of expandable member 20, or to a location at or near a distal end of expandable member 20. In some such examples, the distal extension of inner liner 18 is adhered or otherwise coupled to the inner surface of expandable member 20, or to the outer surface thereof, or otherwise coupled to expandable member 20.

In some examples, a distal portion of elongated body 12 and a proximal portion of expandable member 20 includes a tie layer 38 configured to retain both a distal portion of outer jacket 24 and a proximal portion of expandable member 20 in place overtop of inner liner 18 and inner layer 64 of flexible membrane 48, respectively. However, tie layer 38 may be absent in some other examples.

As in the example illustrated in FIG. 3, expandable member 20 when in its expanded state can have a proximal section 20A, a tapering section 20B, and a distal section 20C. Proximal section 20A can have an inner diameter and/or outer diameter that is substantially equal to the inner and/or outer diameter(s) of distal portion 16B of elongated body 12, even when expandable member 20 is in the expanded state as shown in FIG. 3. Distal section 20C (e.g., a distal-most section of expandable member 20), when in the expanded state, has a larger inner diameter and outer diameter than distal portion 16B of elongated body 12. Distal section 20C can be configured to be generally cylindrical, with a constant or substantially constant inner diameter and/or outer diameter along its length. The length of distal section 20C can be 0.5 cm to about 3 cm, or 0.5 cm to about 2.5 cm, to facilitate engulfing a thrombus during use (without being so long as to generate unacceptable levels of friction during delivery to a patient through a surrounding catheter or sheath). Expandable member 20 (e.g. distal section 20C thereof) can be configured to be self-expanding, e.g. upon advancement beyond the end of a surrounding catheter.

The inside and/or outside diameter of distal section 20C (in the expanded state) can be established by heat-setting expandable braid 70 on a generally cylindrical mandrel having a mandrel diameter approximately equal to the desired expanded-state inside diameter of expandable member 20. In this manner, the expanded-state inside and/or outside diameter of distal section 20C can be selected to enable distal section 20C to make firm contact with the vessel wall when expanded, and provide a large distal mouth 62 for application of high suction force to a thrombus or other material to be aspirated. However, it can also be desirable not to allow the expanded-state inside and/or outside diameter of distal section 20C to become too large, as this can make it difficult to advance catheter 10 through a surrounding catheter or sheath during insertion into a patient (as an aggressively expansive expandable member 20 generates high friction forces against the inner wall of the surrounding catheter or sheath). Consequently, the expanded-state outside diameter of distal section 20C can be about 150 percent to about 300 percent of the outside diameter of distal portion 16B of elongated body 12 (or of the outside diameter of proximal section 20A of expandable member 20). In some examples, the expanded-state outer diameter of distal section 20C can be about 110 percent, 120 percent, 150 percent, 200 percent, 250 percent, or 300 percent of the outside diameter of distal portion 16B of elongated body 12 (or of the outside diameter of the proximal end of expandable member 20). In some examples, an outer diameter of the distal section 20C (e.g., a cylindrical tube) is no more than 300 percent of the outer diameter of the distal body portion 16B.

Figure 4:
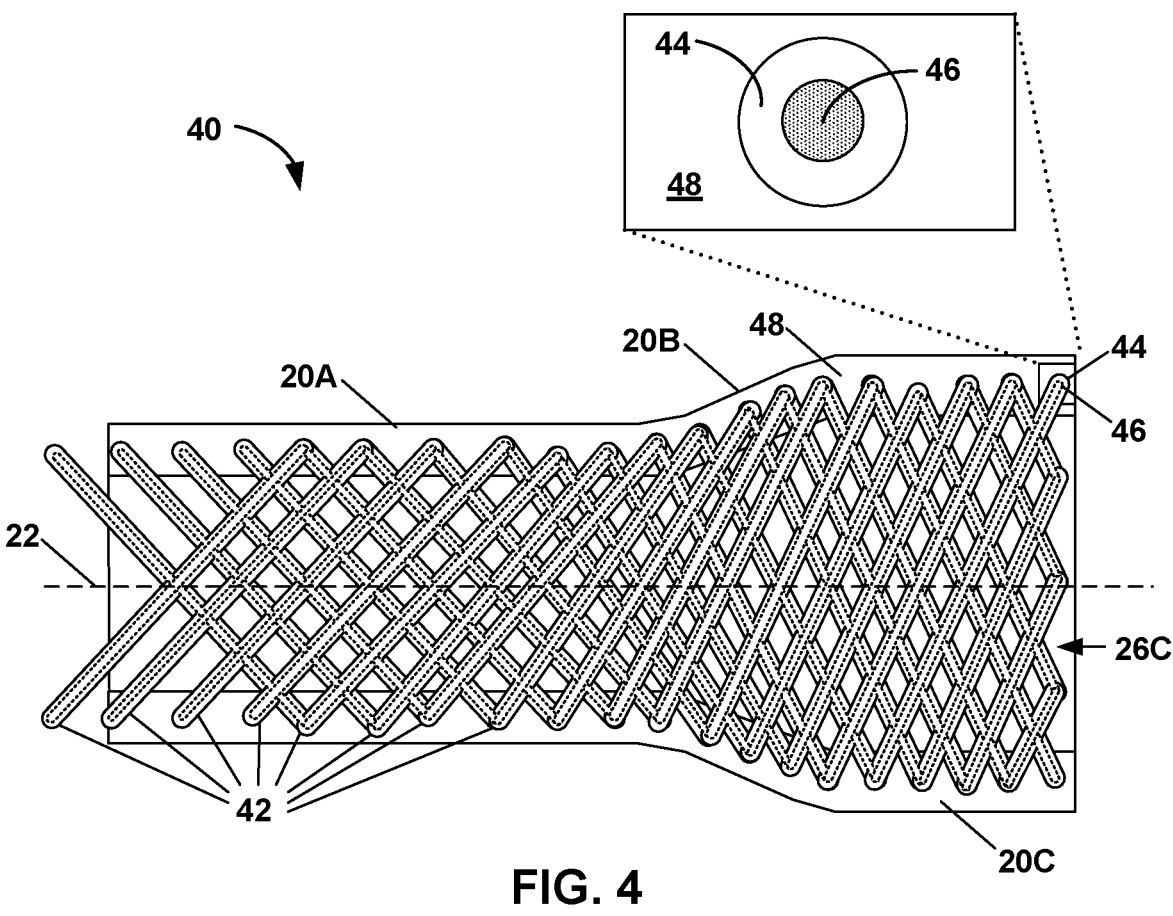
FIGS. 4 and 5 are conceptual cross-sectional views of two examples of an expandable member of the catheter of FIG. 1, where the cross-section is taken through a center of the catheter and along a longitudinal axis.
Figure 5:
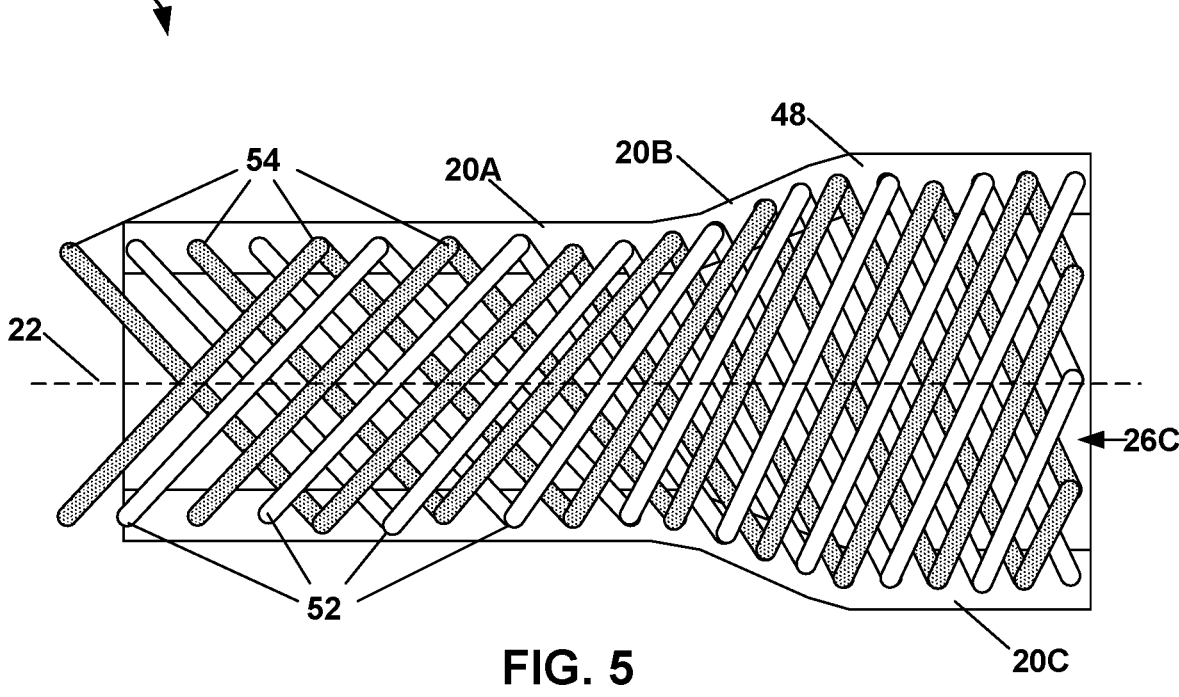

FIGS. 4 and 5 are conceptual cross-sectional views of two examples of expandable member 20 of FIGS. 1-3, where the cross-section is taken through a center of the respective expandable member and along longitudinal axis 22. FIG. 4 depicts example expandable member 40, which can be an example of expandable member 20 of FIGS. 1-3. Expandable member 40 includes a plurality of elongated filaments 42 that are braided (e.g., interwoven) together to form a cylindrical or tubular structure (e.g., a structure defining a lumen 26C within). Some or all of elongated filaments 42 can include at least two different materials, at least one of which is radiopaque. For example, some or all of filaments 42 may include an outer tube 44 comprising a first material, surrounding an inner core 46 comprising a second material, wherein either the first material of the outer tube 44, the second material of the inner core 46, or both, is radiopaque. In examples in which the first material of the outer tube 44 is radiopaque, the first material may be more radiopaque than the second material of the inner core 46. In examples in which the second material of the inner core 46 is radiopaque, the second material may be more radiopaque than the first material of the outer tube 44. In examples in which both the first material and the second material are radiopaque, the first material and the second material may have the approximately the same or different radiopacities.

As one illustrative example, one or more of the elongated filaments 42 of the expandable frame (when braided or woven) may include a drawn-filled tube (DFT) including an outer tube 44 comprising a nickel-titanium alloy (e.g., Nitinol), or stainless steel, or a cobalt-chromium alloy, surrounding an inner core 46 made of a second material that is radiopaque, for example, a material that is more radiopaque than Nitinol, stainless steel or cobalt-chromium alloy (e.g., more radiopaque than the first material). In some examples, the radiopaque second material of the inner core 46 comprises platinum or a platinum alloy. The nickel-titanium alloy may provide expandable member 40 with the desired mechanical strength and shape memory, while platinum or other more radiopaque material provides expandable member 40 with the desired radiopaque properties.

As another non-limiting, illustrative example, one or more of the elongated filaments 42 may include an outer tube 44 comprising a first material, e.g., a gold plating, covering the exterior surface of an inner core 46 comprising a second material, e.g., a Nitinol wire. For example, the first material may be added to an exterior surface of the second material via electro plating or another suitable technique. In some such examples, the first material of the outer tube 44 is more radiopaque than the second material of the inner core 46. However, these examples are not intended to be limiting. Some or all of elongated filaments 42 may include any two suitable materials in which an outer tube 44 comprising the first material is disposed radially outward from an inner core 46 comprising the second material, and at least one of the two materials is radiopaque and more radiopaque than the other material. In this configuration of expandable member 40, the at least one radiopaque material extends throughout a substantial portion of the axial or longitudinal length of expandable member 40 (e.g., along central longitudinal axis 22), thereby enabling expandable member 40 to be radiopaque along its length.

In other examples, such as examples in which the radiopaque material is added via electroplating, the radiopaque material may be placed only at certain locations or intervals along the length of expandable member 20, rather than along the entire axial length. For example, expandable member 20 may include a relatively short (e.g., about 0.1 mm-long) section of gold plating (or other outer material 44) placed at periodic intervals (e.g., at every 1 mm-long interval) along the axial length of the "core" material 46. Some such examples may allow more flexibility of the structural supports (e.g., the inner core 46), compared to examples in which the entire inner core 46 is plated or otherwise covered with outer tube 44.

FIG. 5 depicts another example expandable member 50, which is an example of expandable member 20 of FIGS. 1-3. Expandable member 50 includes a first plurality of elongated filaments 52 that are braided (e.g., interwoven) with a second plurality of elongated filaments 54 to form a cylindrical or tubular structure (e.g., a structure defining a lumen 26C within). Each elongated filament of the first plurality 52 comprises a first material, and each elongated filament of the second plurality 54 comprises a second material, wherein either the first material, the second material, or both is radiopaque. Regardless of whether the second material is radiopaque, however, the first material of the first plurality 52 is more radiopaque than the second material of the second plurality 54 to provide expandable member 50 with the desired radiopacity properties. The first material extends throughout the axial or longitudinal length of expandable member 50, enabling the advantages of catheter 10, as described above with respect to FIGS. 1 and 2.

As one illustrative example of expandable member 50, elongated filaments of the first plurality 52 comprise a first material, such as platinum or platinum alloy, and elongated filaments of the second plurality 54 comprise a second material, such as Nitinol, stainless steel or cobalt-chromium alloy. However, this example is not intended to be limiting.

Figures 6A, 6B:
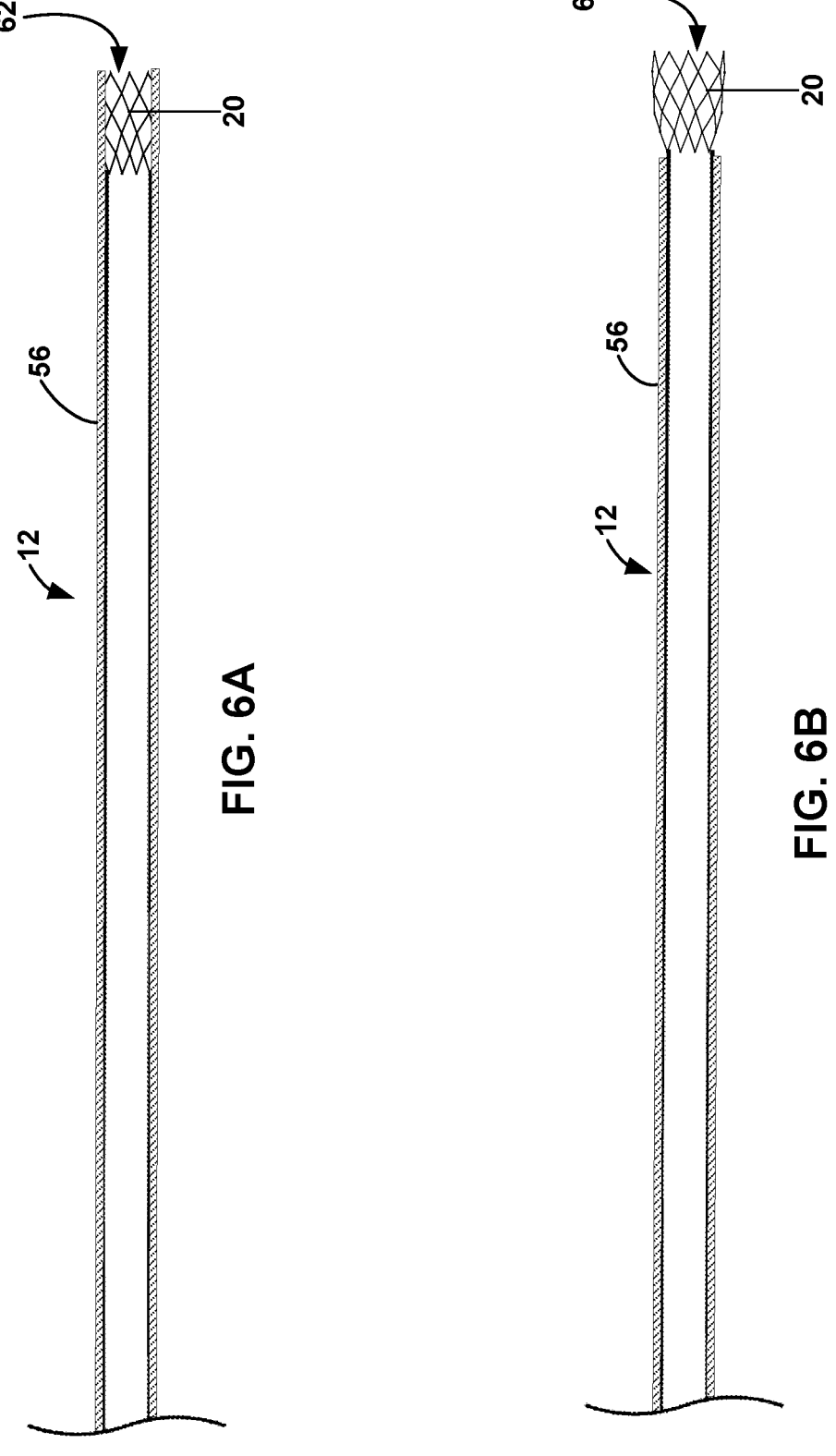
FIGS. 6A and 6B are conceptual cross-sectional side views of an example catheter, which includes an introducer sheath.

FIGS. 2-5 illustrate liquid impermeable layer or flexible membrane 48, which can be, for example, radially inward of the expandable frame of the respective expandable member 20, 40, 50 (e.g., defining an innermost surface of the expandable member), radially outward of the respective expandable member 20, 40, 50 (e.g., defining an outermost surface of the expandable member), or any combination thereof. Membrane 48 can be configured to help ensure that catheter 10 can maintain vacuum pressure when the expandable member is engaged with a thrombus, and also to prevent leakage from inner lumen 26C of the expandable member. Membrane 48 may have a relatively low flexural stiffness to allow for easy bending, and relatively high elongation properties such that the respective expandable member may be necked down (e.g., collapsed into a contracted or delivery configuration) to fit into a sheath (FIGS. 6A and 6B). Some example materials for flexible membrane 48 include polymers such as, but not limited to, polyether-based thermoplastic polyurethanes (TPUs) (e.g., Tecoflex™ or Tecothane™, both available from the Lubrizol Corporation of Wickliffe, Ohio; or Polyblend™, available from Custom Building Products of Santa Fe Springs, California), olefin block copolymer elastomer (available from RTP Company of Winona, Minnesota, or from Foster Corporation of Putnam, Connecticut), silicone, or other similar materials. In some examples, membrane 48 is formed from a fluid-impermeable polymer.

In some examples, flexible membrane 48 is formed from a softer, more flexible material than inner liner 18 and/or outer jacket 24 to enable expandable member 20 to accommodate the expansion of expandable member 20. In some examples, flexible membrane 48 may have a lower coefficient of friction and/or a lower modulus of elasticity, than inner liner 18. The stiffness of flexible membrane 48 can be measured by, for example, a flexural stiffness or a torsional stiffness value. An inner liner 18 which is more stiff than membrane 48 may enable catheter 10 to exhibit a more flexible tip while still retaining sufficient strength and rigidity throughout the majority of elongated body 12 for navigation.

In some examples, the one or more materials from which flexible membrane 48 is formed may be selected to provide better engagement (e.g., mechanical or chemical engagement) with the thrombus. Additionally or alternatively, flexible membrane 48 may include a surface treatment that provides better engagement with a thrombus (e.g., mechanical or chemical engagement).

In some examples, membrane 48 may be formed by reflowing an extruded tube over the braided or coiled structure of the expandable frame of the respective expandable member, or may be formed by dip-coating the expandable frame into the desired material of membrane 48. In some examples, membrane 48 may include a hydrophilic coating on an exterior surface of membrane 48 to provide lubricity for navigating the patient's vasculature.

In some examples, instead of or in addition to the more-rigid structure elements (e.g., outer tube 44, inner core 46, first filaments 52, and/or second filaments 54) of expandable member 20 being radiopaque, membrane 48 may itself include a radiopaque material, such as, but not limited to, one or more of Tungsten, Bismuth Subcarbonate, Tantalum, or Barium Sulfate. For example, in some cases, some or all of the radiopaque visibility of expandable member 20 may be derived from the membrane 48, reducing or abrogating the need for the more-rigid support structure of expandable member 20 to be radiopaque at all. As one illustrative example, membrane 48 may include a thermoplastic elastomer (TPE) that is combined (e.g., compounded) with a radiopaque material, such as about 80% Tungsten (e.g., 80% Tungsten or nearly 80% Tungsten to the extent permitted by manufacturing tolerances). The thermoplastic elastomer and the radiopaque material may be combined together to define a composite material or a mixture. In other examples, membrane 48 may be radiopaque so as to further improve the visibility of expandable member 20. In some examples, membrane 48 may include a distal extension of inner liner 18 and/or outer jacket 24 (FIG. 2) of elongated body 12.

In some examples, catheter 10 may be introduced into the vasculature of a patient with the aid of an introducer sheath, which defines a pathway from an exterior access point into the vasculature (e.g., a radial artery or a femoral artery of the patient). For example, FIGS. 6A and 6B are conceptual cross-sectional side views of expandable member 20 of catheter 10 (FIGS. 1 and 2) being deployed with the aid of an introducer sheath 56. For illustrative purposes, FIGS. 6A and 6B illustrate expandable member 20, and the details of inner liner 18, structural support member 28, and outer jacket 24 are not labeled. FIG. 6A illustrates expandable member 20 in a collapsed configuration within introducer sheath 56 positioned over expandable member 20. Introducer sheath 56 may include a tubular body configured to receive catheter 10.

In some examples, a clinician may position introducer sheath 56 from an incision site (e.g., a femoral access site or a radial access site) and into a patient's vasculature and then introduce catheter 10 into the vasculature through introducer sheath 56. In some examples, catheter 10 is introduced directly into the vasculature via introducer sheath 56. In examples in which expandable member 20 is self-expandable, expandable member 20 is deployed into the expanded configuration (also referred to herein as a deployed configuration) once it exits a distal opening of introducer sheath 56 (as shown in FIG. 6B). A clinician may then navigate catheter 10 through the vasculature of the patient while expandable member 20 is already in the deployed configuration shown in FIG. 6B.

In other examples, catheter 10 may be positioned without an outer catheter that holds expandable member 20 in a collapsed configuration until the expandable member 20 reaches a target site within vasculature of a patient. In some of these examples, a clinician may introduce the outer catheter (in which catheter 10 is positioned) into the vasculature via introducer sheath 56.

Figure 7:
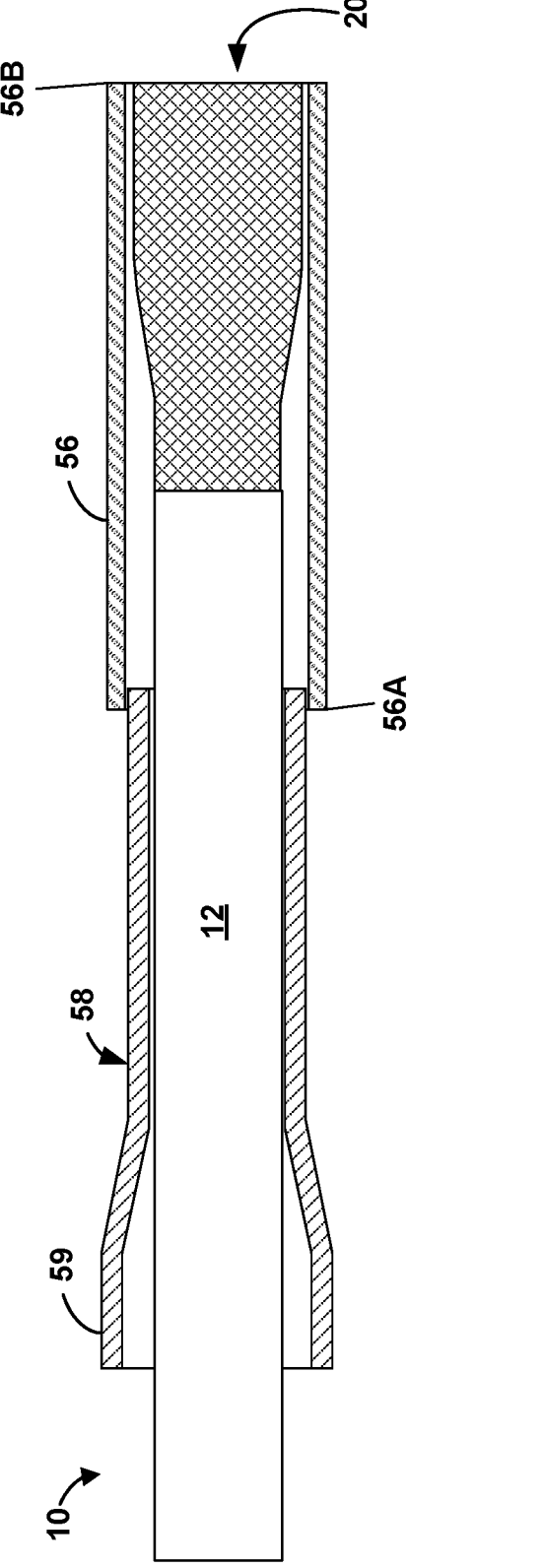
FIG. 7 is a conceptual cross-sectional view of a medical device system including a catheter and an insertion tool.

Catheter 10 may be loaded into introducer sheath 56 directly or with the aid of an insertion tool 58, an example of which is shown in FIG. 7. As described above with respect to FIGS. 1 and 2, an advantage of incorporating a radiopaque material throughout the structure of expandable member 20 and eliminating a more rigid solid metal marker band at the distal tip or portion 60 of catheter 10 is that expandable member 20 may be easily necked down or collapsed to fit within introducer sheath 56. As shown in FIG. 7, insertion tool 58 (also referred to as an "introducer tool" or a "compression tool") is configured to collapse expandable member 20 into a collapsed or delivery configuration and enable expandable member 20 to fit within an inner lumen of introducer sheath 56. Expandable member 20 may be introduced into funnel 59 at one end of insertion tool 58, and as expandable member 20 is pushed into insertion tool 58, funnel 59 collapses expandable member 20 into a collapsed configuration.

A clinician may use introducer tool 58 to insert expandable member 20 into introducer sheath 56, e.g., during a medical procedure or in preparation for the medical procedure. The clinician may, for example, use introducer tool 58 to collapse expandable member 20 (or expandable member 20 may be preloaded within introducer tool 58 at the time of manufacture), and then push distal tip or portion 60 of catheter 10 from insertion tool 58 into proximal end 56A of introducer sheath 56 and towards distal end 56B of introducer sheath 56.

Insertion tool 58 may be formed from any suitable material, such as, but not limited to, polytetrafluoroethylene (PTFE).

FIG. 8 is a flow diagram of an example method of aspiration using catheter 10 of FIGS. 1 and 2. The techniques of FIG. 8 include inserting catheter 10 into vasculature of the patient (80), deploying expandable member 20 to expand expandable member 20 in the vasculature of the patient (82), and aspirating a thrombus (84). In some examples, the techniques described herein include removing catheter 10 from the vasculature of the patient once the procedure is complete. Throughout the techniques of FIG. 8, a clinician may observe a radiopaque material of expandable member 20 via fluoroscopic imaging to improve surgical performance and patient outcomes.

A clinician may observe, using fluoroscopic imaging, expandable member 20 while distally advancing distal tip or portion 60 of catheter 10 toward a target site. In some examples, inserting catheter 10 into vasculature of a patient (80) may include initially introducing a guidewire, guide catheter, or another guide member into the vasculature of the patient to a target treatment site. Elongated body 12 may then be introduced over the guidewire and advanced to the target treatment site. Additionally, or alternatively, catheter 10 may be introduced into vasculature of a patient with the aid of a guide catheter. For example, the guide catheter may be initially introduced into vasculature of a patient and positioned adjacent a target treatment site. Catheter 10 may then be introduced through an inner lumen of the guide catheter.

Once within the vasculature, expandable member 20 may be deployed into the vasculature (82). In some examples, expandable member 20 may be self-expanding and may expand without the aid of any additional expansion mechanisms once released from introducer sheath 56 or another outer sheath. Additionally, or alternatively, expandable member 20 may be expanded using a balloon. In other examples, expandable member may be expanded by applying electrical energy to expandable member 20. For example, expandable member 20 (or a portion or layer thereof) may be constructed using a shape memory alloy actuator material.

The technique of FIG. 8 also includes applying a suction force to inner lumen 26 of catheter 10 to remove a thrombus from the vasculature (84). For example, once distal tip or portion 60 of catheter 10 is positioned proximate to a thrombus, a clinician may actuate a suction source to apply a suction force to lumen 26. The suction source can comprise a pump, such as a direct-acting pump (e.g., a peristaltic pump, or a lobe, vane, gear, or piston pump, or other suitable pumps of this type) or an indirect-acting pump (e.g., a vacuum pump, which creates a partial vacuum in an evacuation volume fluidically coupled to the liquid to be displaced). Due to the radiopacity of expandable member 20, a clinician may observe or determine, using fluoroscopic imagery, a longitudinal or axial contraction of expandable member 20 during the aspiration, as well as a shape of expandable member 20, which may indicate that the expandable member 20 is in engaged with the thrombus.

In some examples, the suction force applied to inner lumen 26 of catheter 10 is varied over time, referring to herein as cyclical aspiration. As discussed above, during this cyclical aspiration, expandable member 20 may axially compress and expand in response to the varying suction force.

Catheter 10 may be removed from the vasculature once the aspiration procedure is complete.

Various aspects of the disclosure have been described. These and other aspects are within the scope of the following claims.

What is claimed is:

1. A catheter comprising:

an elongated body comprising a proximal body portion and a distal body portion, and defining a body inner lumen; and an expandable member located at the distal body portion, the expandable member defining an expandable member inner lumen, the expandable member inner lumen comprising a distal extension of the body inner lumen, wherein the expandable member is configured to self-expand radially outward from a collapsed configuration to an expanded configuration and thereby expand the expandable member inner lumen radially outward, wherein the expandable member comprises a plurality of structural elements, one or more of the structural elements of the plurality of structural elements comprising a first material surrounding a core comprising a second material, wherein the first material is more radiopaque than the second material, or wherein the second material is more radiopaque than the first material, wherein at least one of the first material or the second material comprises a shape memory material, wherein the expandable member comprises a flexible membrane having a stiffness that is less than a stiffness of at least one of an outer jacket or an inner liner of the elongated body, wherein the elongated body further comprises:

the inner liner;

the outer jacket; and a structural support member positioned between the inner liner and the outer jacket, wherein a proximal portion of the plurality of structural elements of the expandable member longitudinally overlap and is radially outward of an outer surface of a distal portion of the structural support member of the elongated body, wherein the proximal portion of the plurality of structural elements of the expandable member and the outer surface of the distal portion of the structural support member are separated by a tie layer, and wherein the expandable member is configured to, during application of a suction force to the body inner lumen, axially contract in response to sealing contact with a thrombus enabling a user to observe, via fluoroscopic imagery, that the catheter is engaged with the thrombus.

2. The catheter of claim 1, wherein the expandable member defines a cylindrical tube when in the expanded configuration, wherein when the expandable member is in the expanded configuration, an outer diameter of the cylindrical tube is greater than an outer diameter of the distal body portion, and wherein the outer diameter of the cylindrical tube is no more than 300% of the outer diameter of the distal body portion.

3. The catheter of claim 1, wherein the first material comprises an electroplated coating on an exterior surface of the core.

4. The catheter of claim 1, wherein one or more structural elements of the plurality of structural elements comprises a drawn-filled tube.

5. The catheter of claim 1, wherein the plurality of structural elements comprises filaments interwoven into a braided structure.

6. The catheter of claim 1, wherein the plurality of structural elements comprises struts defining an expandable frame.

7. The catheter of claim 1, wherein the catheter does not have a solid metal radiopaque marker band distal to a proximal end of the expandable member.

8. The catheter of claim 1, wherein the first material comprises a nickel-titanium alloy, and wherein the second material comprises platinum or a platinum alloy.

9. The catheter of claim 1, wherein the first material comprises gold, and the second material comprises a nickel-titanium alloy.

10. The catheter of claim 1, wherein the flexible membrane is coupled to the plurality of structural elements.

11. The catheter of claim 1, wherein the flexible membrane is radiopaque.

12. A system comprising:
an introducer sheath;
the catheter of claim 1; and
a compression tool configured to compress the expandable member for insertion of the catheter into the introducer sheath.

13. The catheter of claim 1, wherein a diameter of a distal end of the expandable member is less than a diameter of the thrombus.

14. The catheter of claim 1, wherein the expandable member is configured to, during application of the suction force to the body inner lumen, maintain the expanded configuration in an absence of sealing contact with the thrombus.

15. The catheter of claim 1,
wherein the expandable member, when in the expanded configuration, includes a tapering section and a distal section distal to the tapering section, and
wherein the inner liner of the elongated body terminates at or proximal to the tapering section of the expandable member.

16. A catheter comprising:
an elongated body including a proximal body portion and a distal body portion, and defining a body inner lumen; and
a radiopaque expandable member located at the distal body portion of the elongated body, the expandable member defining an expandable member inner lumen in fluid communication with the body inner lumen,
wherein the expandable member is configured to self-expand radially outward from a collapsed configuration to an expanded configuration,
wherein the expandable member comprises a plurality of structural elements,
wherein the expandable member comprises a shape memory material,
wherein the expandable member comprises a flexible membrane having a stiffness that is less than a stiffness of at least one of an outer jacket or an inner liner of the elongated body,
wherein the elongated body further comprises:
the inner liner;
the outer jacket; and
a structural support member positioned between the inner liner and the outer jacket, wherein a proximal portion of the plurality of structural elements of the expandable member longitudinally overlap and is radially outward of an outer surface of a distal portion of the structural support member of the elongated body,
wherein the proximal portion of the plurality of structural elements of the expandable member and the outer surface of the distal portion of the structural support member are separated by a tie layer, and
wherein the expandable member is configured to, during application of a suction force to the body inner lumen, axially contract in response to sealing contact with a thrombus enabling a user to observe, via fluoroscopic imagery, that the catheter is engaged with the thrombus.

17. The catheter of claim 16, wherein one or more of the structural elements of the plurality of structural elements comprising a first material surrounding a core comprising a second material, and wherein the first material is more radiopaque than the second material, or wherein the second material is more radiopaque than the first material.

18. The catheter of claim 16, wherein the expandable member is configured to be navigated through vasculature of the patient while the expandable member is in the expanded configuration.

19. The catheter of claim 16, wherein the flexible membrane is coupled to a plurality of structural elements, and wherein the flexible membrane comprises a thermoplastic elastomer combined with a radiopaque material.

20. The catheter of claim 16,
wherein the expandable member comprises a plurality of first filaments comprising a first material interwoven with a plurality of second filaments comprising a second material, and
wherein the second material is more radiopaque than the first material.

21. The catheter of claim 20, wherein the catheter does not comprise a solid metal radiopaque marker band at the distal body portion of the elongated body.

22. The catheter of claim 16, wherein the tie layer is configured to retain the outer jacket and the proximal portion of the plurality of structural elements of the expandable member in place overtop of the inner liner.

23. A catheter comprising:
an elongated body comprising a proximal body portion and a distal body portion, and defining a body inner lumen; and
an expandable member located at the distal body portion, the expandable member defining an expandable member inner lumen, the expandable member inner lumen comprising a distal extension of the body inner lumen,
wherein the expandable member is configured to self-expand radially outward from a collapsed configuration to an expanded configuration and thereby expand the expandable member inner lumen radially outward,
wherein the expandable member comprises a plurality of structural elements, one or more of the structural elements of the plurality of structural elements comprising a first material surrounding a core comprising a second material,
wherein the first material is more radiopaque than the second material, or wherein the second material is more radiopaque than the first material,
wherein at least one of the first material or the second material comprises a shape memory material, wherein the expandable member comprises a flexible membrane having a stiffness that is less than a stiffness of at least one of an outer jacket or an inner liner of the elongated body, wherein the elongated body further comprises:

the inner liner;

the outer jacket; and a structural support member positioned between the inner liner and the outer jacket, wherein a proximal portion of the plurality of structural elements of the expandable member longitudinally overlap and is radially outward of an outer surface of a distal portion of the structural support member of the elongated body, wherein the proximal portion of the plurality of structural elements of the expandable member and the outer surface of the distal portion of the structural support member are separated by a tie layer, and wherein the expandable member is configured to axially contract in response to an application of a suction force to the proximal body portion of the elongated body.

24. The catheter of claim 23, wherein the expandable member is configured to, during application of the suction force to the body inner lumen, maintain the expanded configuration.

\* \* \* \* \*